(12) United States Patent
Qiu

(10) Patent No.: US 6,753,380 B2
(45) Date of Patent: Jun. 22, 2004

(54) WATER-AND OIL-REPELLENCY IMPARTING ESTER OLIGOMERS COMPRISING PERFLUOROALKYL MOIETIES

(75) Inventor: Zai-Ming Qiu, Woodbury, MN (US)

(73) Assignee: 3M Innovative Properties Company, Saint Paul, MN (US)

(*) Notice: Subject to any disclaimer, the term of this patent is extended or adjusted under 35 U.S.C. 154(b) by 461 days.

(21) Appl. No.: 09/803,708

(22) Filed: Mar. 9, 2001

(65) Prior Publication Data

US 2003/0001130 A1 Jan. 2, 2003

(51) Int. Cl.[7] .............. C08L 67/02; B32B 9/00; B32B 27/00
(52) U.S. Cl. ............ 525/200; 525/199; 525/276; 526/243; 526/248; 526/242; 428/411.1; 428/357; 523/200; 524/539; 524/168; 524/462
(58) Field of Search ................ 523/200; 524/539, 524/168, 462; 252/8.05, 183.11; 525/199, 200, 276; 526/243, 248, 242

(56) References Cited

U.S. PATENT DOCUMENTS

| | | |
|---|---|---|
| 2,803,615 A | 8/1957 | Ahlbrecht et al. |
| 2,803,656 A * | 8/1957 | Ahlbrecht .................... 564/96 |
| 3,068,187 A | 12/1962 | Bolstad et al. |
| 3,094,547 A | 6/1963 | Heine |
| 3,102,103 A | 8/1963 | Ahlbrecht et al. |
| 3,341,497 A | 9/1967 | Sherman et al. |
| 3,478,116 A | 11/1969 | Smeltz |
| 3,574,791 A | 4/1971 | Sherman et al. |
| 3,734,962 A * | 5/1973 | OlsNiederprum et al. ..... 564/96 |
| 3,787,351 A * | 1/1974 | Olson ......................... 523/453 |
| 3,916,053 A | 10/1975 | Sherman et al. |
| 3,987,182 A | 10/1976 | Gold |
| 3,987,227 A | 10/1976 | Schultz et al. |
| 4,160,777 A | 7/1979 | Loudas |
| 4,215,205 A | 7/1980 | Landucci |
| 4,426,466 A | 1/1984 | Schwartz |
| 4,468,527 A | 8/1984 | Patel |
| 4,504,401 A | 3/1985 | Matsuo et al. |
| 4,508,916 A | 4/1985 | Newell et al. |
| 4,529,658 A | 7/1985 | Schwartz et al. |
| 4,533,713 A | 8/1985 | Howells |
| 4,540,765 A | 9/1985 | Koemm et al. |
| 4,566,981 A | 1/1986 | Howells |
| 4,606,737 A | 8/1986 | Stern |
| 4,668,406 A | 5/1987 | Chang |
| 4,958,039 A | 9/1990 | Pechhold |
| 5,025,052 A | 6/1991 | Crater et al. |
| 5,115,013 A | 5/1992 | Röttger et al. |
| 5,145,727 A | 9/1992 | Potts et al. |
| 5,149,576 A | 9/1992 | Potts et al. |
| 5,204,441 A | 4/1993 | Baum et al. |
| 5,216,097 A | 6/1993 | Allewaert et al. |
| 5,276,175 A | 1/1994 | Dams et al. |
| 5,414,102 A | 5/1995 | Pohmer et al. |
| 5,424,474 A | 6/1995 | Pohmer et al. |
| 5,451,622 A | 9/1995 | Boardman et al. |
| 5,674,951 A | 10/1997 | Hargis et al. |
| 5,688,884 A | 11/1997 | Baker et al. |
| 5,725,789 A | 3/1998 | Huber et al. |
| 6,037,429 A | 3/2000 | Linert et al. |
| 6,127,485 A * | 10/2000 | Klun et al. ................. 525/199 |
| 6,174,964 B1 * | 1/2001 | Jariwala et al. ............. 525/276 |
| 6,238,798 B1 * | 5/2001 | Kang et al. .................. 428/421 |
| 6,288,157 B1 * | 9/2001 | Jariwala et al. ............. 524/462 |
| 6,582,759 B1 * | 6/2003 | Qiu et al. ................ 427/163.1 |
| 6,586,522 B1 * | 7/2003 | Jariwala et al. ............. 524/539 |

FOREIGN PATENT DOCUMENTS

| | | |
|---|---|---|
| DE | 3611302 A1 | 10/1987 |
| GB | 858671 | 11/1961 |

OTHER PUBLICATIONS

Banks, Ed., Organofluorine Chemicals and Their Industrial Applications, Ellis Horwood Ltd., Chichester, England, pp. 226–234, (1979).
Roger W. Phillips[1] and Robert H. Dettre[2], Application of ESCA and Contact Angle Measurements to Studies of Surface Activity in a Fluoropolymer Mixture, Journal of Colloid and Interface Science, vol. 56, No. 2, Aug. (1976).
Murray Hauptschein[1a] and Robert A. Braun[1b], The Reaction of Ethyl Perfluorobutyrate with Sodium, an Improved Synthesis of Perfluoroheptan–4–one, JACS, vol. 77, pp. 4930–4931, (1955).
E. T. McBee, W. F. Marzluff and O. R. Pierce, The Ionization Constants of Some Fluorine–Containing Alcohols[1,2], Journal of American Chemistry Society, vol. 74, pp. 444–446, (1952).
J. L. Zollinger, J. R. Throckmorton, S. T. Ting, and R. A. Mitsch, Preparation and Curing Of Poly (Perfluoroalkylene Oxides), J. Macromol. Sci.–Chem., A3(7), pp. 1443–1464, Nov. (1969).
Technical Manual & Yearbook of The American Association of Textile Chemists & Colorists (AATCC), AATCC Test Method 22, pp. 70–71, (1985).
Van A. Wente, Superfine Thermoplastic Fibers, Industrial and Engineering Chemistry, vol. 48, No. 8, pp. 1342–1346, Aug. (1956).
U.S. patent application Ser. No. 09/592,105, Jariwala et al., filed Jun. 12, 2000, "Water– And Oil– Repellent Composition", pp. 1–91.
U.S. patent application Ser. No. 09/803,702, Qiu, filed Mar. 9, 2001, Water–and Oil–Repellency Imparting Urethane Oligomers Comprising Perfluoroalkyl Moieties, pp. 1–87.

* cited by examiner

Primary Examiner—Joseph D. Anthony
(74) Attorney, Agent, or Firm—Kent S. Kokko

(57) ABSTRACT

Fluorochemical ester compositions comprising one or more compounds or oligomers having at least on fluorine-containing repeatable unit and at least one fluorine-containing terminal group are described. The compositions are useful as coatings or incorporated as melt additives. The fluorochemical compositions impart oil and water repellency to the substrate. In other aspects, this invention relates to processes for imparting oil and water repellency characteristics to substrates and articles.

30 Claims, No Drawings

WATER-AND OIL-REPELLENCY IMPARTING ESTER OLIGOMERS COMPRISING PERFLUOROALKYL MOIETIES

FIELD OF THE INVENTION

This invention relates to fluorochemical compositions comprising one or more compounds or oligomers having at least one fluorine-containing repeatable unit and at least one fluorine-containing terminal group. This invention also relates to articles comprising a substrate and the fluorochemical composition, which may be applied as coatings or incorporated as melt additives the fluorochemical compositions impart oil and water repellency to the substrate. In other aspects, this invention relates to processes for imparting oil and water repellency characteristics to substrates and articles.

BACKGROUND OF THE INVENTION

The use of certain fluorochemical compositions on fibers and fibrous substrates, such as textiles, paper, and leather, to impart oil- and water-repellency and soil- and stain-resistance is well known in the art. See, for example, Banks, Ed., Organofluorine Chemicals and Their Industrial Applications, Ellis Horwood Ltd., Chichester, England, 1979, pp. 226–234. Such fluorochemical compositions include, for example, fluorochemical guanidines (U.S. Pat. No. 4,540,497, Chang et al.), compositions of cationic and non-cationic fluorochemicals (U.S. Pat. No. 4,566,981, Howells), compositions containing fluorochemical carboxylic acid and epoxidic cationic resin (U.S. Pat. No. 4,426,466, Schwartz), fluoroaliphatic carbodiimides (U.S. Pat. No. 4,215,205, Landucci), fluoroaliphatic alcohols (U.S. Pat. No. 4,468,527, Patel), fluorine-containing addition polymers, copolymers, and macromers (U.S. Pat. Nos. 2,803,615; 3,068,187; 3,102,103; 3,341,497; 3,574,791; 3,916,053; 4,529,658; 5,216,097; 5,276,175; 5,725,789; 6,037,429), fluorine-containing phosphate esters (U.S. Pat. Nos. 3,094,547; 5,414,102; 5,424,474), fluorine-containing urethanes (U.S. Pat. Nos. 3,987,182; 3,987,227; 4,504,401; 4,958,039), fluorochemical allophanates (U.S. Pat. No. 4,606,737) fluorochemical biurets (U.S. Pat. No. 4,668,406), fluorochemical oxazolidinones (U.S. Pat. No. 5,025,052), and fluorochemical piperazines (U.S. Pat. No. 5,451,622).

It has long since been well documented that the fluorochemical segment, $F(CF_2)_n$—, of essentially any oil- and water-repellency imparting compound, oligomer, or polymer must have six or more carbon atoms; that is n must be equal to or greater than 6 (Philips, R. W. and Dettre, R. H., J. Col. and Interface Sci., 56 (2), (1976)). However, the use of such prior art fluorochemical compositions having fluorochemical segments with n>6, has been cited as a potential concern. Many previously known oil- and water-repellency imparting compounds or oligomers contain perfluorooctyl moieties. These surfactants ultimately degrade to perfluorooctyl-containing compounds. It has been reported that certain perfluorooctyl-containing compounds may tend to bio-accumulate in living organisms; this tendency has been cited as a potential concern regarding some fluorochemical compounds. For example, see U.S. Pat. No. 5,688,884 (Baker et al.). As a result, there is a desire for fluorine-containing compositions which are effective in providing desired oil and water repellency, and/or stain-release or stain resistance properties, and which eliminate more effectively from the body (including the tendency of the composition and its degradation products).

SUMMARY OF THE INVENTION

In one aspect, this invention relates to chemical compositions comprising one or more compounds or oligomers having at least one fluorine-containing repeatable unit and at least one fluorine-containing terminal group. These compounds or oligomers comprise the condensation reaction product of (a) one or more polyols; (b) one or more polyacyl compounds (such as carboxylic acids, esters, acyl halides); and (c) one or more monofunctional fluorine-containing compounds comprising a functional group that is reactive with the hydroxyl group of the polyol (a) or with the acyl group of the polyacyl compound (b); wherein at least a portion of the polyol compounds further comprise at least one fluorine-containing group selected from the group consisting of perfluoroalkyl, perfluoroheteroalkyl, and perfluoroheteroalkylene. Optionally, the fluorochemical oligomers further comprise water-solubilizing groups and/or polymerizable groups.

As used herein, the term "oligomer" means a polymer molecule consisting of only a few, i.e. up to an average of 10, but preferably up to an average of 5, repeating (polymerized) or repeatable units. Each repeating unit comprises an ester group that is derived or derivable from the reaction of at least one polyol having an average of greater than one, preferably two or more hydroxyl moieties; and at least one polyacyl compound having an average of greater than one, preferably two or more acyl moieties, wherein at least a portion of the polyol compounds further comprises at least one fluorine-containing moiety, selected from the group consisting of perfluoroalkyl, perfluoroalkylene, perfluoroheteroalkyl, and perfluoroheteroalkylene. The oligomer is terminated with one or more perfluoroalkyl groups, one or more perfluoroheteroalkyl groups, or mixtures thereof.

Certain preferred embodiments of the fluorochemical compositions of the present invention include those compositions comprising terminal and pendant $R_f$ groups having from 1 to 12 carbons, preferably 6 or fewer carbons, and more preferably three to five carbons. Even with $R_f$ groups that are relatively short (i.e. a carbon chain length of less than eight carbon atoms), these fluorochemical compositions, surprisingly, impart excellent oil and water repellency and stain release or stain resistance and exhibit high dynamic water and hexadecane contact angles. Although compositions comprising low fluorine content are less expensive, $R_f$ groups shorter than eight carbons typically have been overlooked by those of skill in the art because they have been believed to impart inferior oil and water repellency and stain resistance.

When the compounds further comprise water-solubilizing groups, the fluorochemical compositions of the present invention exhibit water solubility or water dispersability, while at the same time providing surprisingly good water-repellency and stain-release properties. These embodiments include, for example, those chemical compositions comprising a ester oligomer containing one or more solubilizing groups. The solubilizing groups include carboxylate, sulfate, sulfonate, phosphate, phosphonate, ammonium, quaternary ammonium, and the like, and mixtures thereof. These embodiments are particularly well suited for uniform topical treatments on a variety of substrates where the use of organic solvents is undesirable.

When the compounds further comprise polymerizable groups, the coatings derived from the fluorochemical compositions of the present invention exhibit increased durability. That is the repellency and stain-resistant properties remain even after abrasion, scrubbing, washing, exposure to wear, and the like.

Another embodiment of the present invention relates to a coating composition comprising a solution comprising the fluorochemical composition of the present invention and a solvent. In this embodiment, the fluorochemical composition is dissolved or dispersed in the solvent. When applied to a substrate, this coating composition provides a uniform distribution of the chemical composition on the substrate without altering the appearance of the substrate. This invention further relates to a method for imparting water- and oil-repellency, stain-release, or stain-resistance characteristics to a substrate, comprised of one or more surfaces, comprising the steps of:

(a) applying the coating composition of the present invention onto one or more surfaces of the substrate wherein the coating composition comprises:

(i) at least one solvent; and (ii) the fluorochemical composition of the invention; and (b) curing the coating composition.

The fluorochemical compositions of the present invention can be applied as coatings to a wide variety of substrates, for example, by topical application, to impart oil- and water-repellency, stain-release, and stain-resistant properties to the substrates. In testing substrates coated with the fluorochemical compositions of the present invention, unexpectedly high dynamic water and hexadecane contact angles have been observed.

When applied as a coating, the chemical compositions of the present invention can provide a uniform film. Applied as a coating, the chemical compositions of the present invention do not change the appearance of the substrate to which they are applied. In addition, with certain chemical compositions of the present invention, there is no need for high temperature curing; they can be cured (i.e., dried) at ambient temperature. Some compositions require higher temperature, i.e. up to about 130° C.

The fluorochemical compositions of the present invention may also be incorporated into a polymer as a polymer melt blend. The polymer composition comprises one or more thermoplastic or thermoset polymers and the fluorochemical composition of the invention. The present invention also relates to a process for preparing a repellent composition comprising the steps of (a) combining the fluorochemical composition and at least one thermoplastic polymer; and (b) melt processing the resulting combination.

The present invention further relates to a process for preparing a repellent composition comprising the steps of (a) combining the fluorochemical composition and at least one thermosetting polymer or ceramer or the reactive precursors of said polymer or ceramer; and (b) curing the resulting combination.

This invention also provides an article comprising a substrate coated or blended with the fluorochemical composition of the invention. After application and curing of the fluorochemical composition on the substrate or melt blending the fluorochemical composition with the substrate, the substrate displays surprisingly high water and hexadecane contact angles which are normally correlated to water- and oil-repellency, stain-release, or stain-resistance properties.

Still further, this invention relates to a method for imparting water- and oil-repellency, stain-release, or stain-resistance characteristics to a shaped article comprising the steps of:

(a) melt blending a fluorochemical composition with one or more thermoplastic polymers and (b) forming the melt blend into a shaped article.

The present invention also relates to a process for preparing a repellent composition comprising the steps of (a) combining a fluorochemical composition and at least one thermoplastic polymer; and (b) melt processing the resulting combination.

Still further, this invention relates to a method for imparting water- and oil-repellency, stain-release, or stain-resistance characteristics to an article comprising the steps of:

(a) melt blending a fluorochemical composition of the present invention with one or more thermoplastic polymers and (b) forming the melt blend into a shaped article;

Definitions

Unless otherwise stated, the following terms used in the specification and claims have the meanings given below:

"Acyloxy" means a radical—OC(O)R where R is, alkyl, alkenyl, and cycloalkyl, e.g., acetoxy, 3,3,3-trifluoroacetoxy, propionyloxy, and the like.

"Alkoxy" means a radical—OR where R is an alkyl group as defined below, e.g., methoxy, ethoxy, propoxy, butoxy, and the like.

"Alkyl" means a linear saturated monovalent hydrocarbon radical having from one to about twelve carbon atoms or a branched saturated monovalent hydrocarbon radical having from three to about twelve carbon atoms, e.g., methyl, ethyl, 1-propyl, 2-propyl, pentyl, and the like.

"Alkylene" means a linear saturated divalent hydrocarbon radical having from one to about twelve carbon atoms or a branched saturated divalent hydrocarbon radical having from three to about twelve carbon atoms, e.g., methylene, ethylene, propylene, 2-methylpropylene, pentylene, hexylene, and the like.

"Aralkylene" means an alkylene radical defined above with an aromatic group attached to the alkylene radical, e.g., benzyl, pyridylmethyl, 1-naphthylethyl, and the like.

"Cured chemical composition" means that the chemical composition is dried or solvent has evaporated from the chemical composition from ambient temperature or higher until dryness, up to approximately 24 hours.

"Fibrous substrate" means materials comprised of synthetic or inorganic fibers such as wovens, knits, nonwovens, carpets, and other textiles; and materials comprised of natural fibers such as cotton, paper, and leather.

"Fluorocarbon monoalcohol" means a compound having one hydroxyl group and a perfluoroalkyl or a perfluoroheteralkyl group, e.g. $C_4F_9SO_2N(CH_3)CH_2CH_2OH$, $C_4F_9CH_2CH_2OH$, $C_2F_5O(C_2F_4O)_3CF_2CONHC_2H_4OH$, $c\text{-}C_6F_{11}CH_2OH$, and the like.

"Hard substrate" means any rigid material that maintains its shape, e.g., glass, ceramic, concrete, natural stone, wood, metals, plastics, and the like.

"Heteroacyloxy" has essentially the meaning given above for acyloxy except that one or more heteroatoms (i.e. oxygen, sulfur, and/or nitrogen) may be present in the R group and the total number of carbon atoms present may be up to 50, e.g., $CH_3CH_2OCH_2CH_2C(O)O—$, $C_4H_9OCH_2CH_2OCH_2CH_2C(O)O—$, $CH_3O(CH_2CH_2O)_nCH_2CH_2C(O)O—$, and the like.

"Heteroalkoxy" has essentially the meaning given above for alkoxy except that one or more heteroatoms (i.e. oxygen, sulfur, and/or nitrogen) may be present in the alkyl chain and the total number of carbon atoms present may be up to 50, e.g. $CH_3CH_2OCH_2CH_2O-$, $C_4H_9OCH_2CH_2OCH_2CH_2O-$, $CH_3O(CH_2CH_2O)_nH$, and the like.

"Heteroalkyl" has essentially the meaning given above for alkyl except that one or more heteroatoms (i.e. oxygen, sulfur, and/or nitrogen) may be present in the alkyl chain, these heteroatoms being separated from each other by at least one carbon, e.g., $CH_3CH_2OCH_2CH_2-$, $CH_3CH_2OCH_2CH_2OCH(CH_3)CH_2-$, $C_4F_9CH_2CH_2SCH_2CH_2-$, and the like.

"Heteroalkylene" has essentially the meaning given above for alkylene except that one or more heteroatoms (i.e. oxygen, sulfur, and/or nitrogen) may be present in the alkylene chain, these heteroatoms being separated from each other by at least one carbon, e.g., $-CH_2OCH_2O-$, $-CH_2CH_2OCH_2CH_2-$, $-CH_2CH_2N(CH_3)CH_2CH_2-$, $-CH_2CH_2SCH_2CH_2-$, and the like.

"Heteroaralkylene" means an aralkylene radical defined above except that catenated oxygen, sulfur, and/or nitrogen atoms may be present, e.g., phenyleneoxymethyl, phenyleneoxyethyl, benzyleneoxymethyl, and the like.

"Halo" means fluoro, chloro, bromo, or iodo, preferably fluoro and chloro.

"Perfluoroalkyl" has essentially the meaning given above for "alkyl" except that all or essentially all of the hydrogen atoms of the alkyl radical are replaced by fluorine atoms and the number of carbon atoms is from 1 to about 12, e.g. perfluoropropyl, perfluorobutyl, perfluorooctyl, and the like.

"Perfluoroalkylene" has essentially the meaning given above for "alkylene" except that all or essentially all of the hydrogen atoms of the alkylene radical are replaced by fluorine atoms, e.g., perfluoropropylene, perfluorobutylene, perfluorooctylene, and the like "Perfluoroheteroalkyl" has essentially the meaning given above for "heteroalkyl" except that all or essentially all of the hydrogen atoms of the heteroalkyl radical are replaced by fluorine atoms and the number of carbon atoms is from 3 to about 100, e.g. $CF_3CF_2OCF_2CF_2-$, $CF_3CF_2O(CF_2CF_2O)_3CF_2CF_2-$, $C_3F_7O(CF(CF_3)CF_2O)_mCF(CF_3)CF_2-$ where m is from about 10 to about 30, and the like.

"Perfluoroheteroalkylene" has essentially the meaning given above for "heteroalkylene" except that all or essentially all of the hydrogen atoms of the heteroalkylene radical are replaced by fluorine atoms, and the number of carbon atoms is from 3 to about 100, e.g., $-CF_2OCF_2-$, $-CF_2O(CF_2O)_n(CF_2CF_2O)_mCF_2-$, and the like.

"Perfluorinated group" means an organic group wherein all or essentially all of the carbon bonded hydrogen atoms are replaced with fluorine atoms, e.g. perfluoroalkyl, perfluoroheteroalkyl, and the like.

"Polyacyl compound" means a compound containing two or more acyl groups, or derivative thereof, such as carboxylic acid, ester, or acyl halide, attached to a multivalent organic group, e.g. dimethyl adipate, and the like.

"Polyol" means an organic compound or polymer with an average of at least about 2 primary or secondary hydroxyl groups per molecule, e.g. ethylene glycol, propylene glycol, 1,6-hexanediol, and the like.

"Porous" means capable of imbibing a liquid.

DETAILED DESCRIPTION OF THE ILLUSTRATIVE EMBODIMENTS OF THE INVENTION

The fluorochemical compositions of the present invention comprise the condensation reaction product of (a) one or more fluorinated polyols; (b) one or more polyacyl compounds (such as carboxylic acids, esters, acyl halides); and (c) one or more monofunctional fluorine-containing compounds comprising a functional group that is reactive with the hydroxyl group of the polyol (a) or the acyl group of the polyacyl compound (b). The fluorinated polyol compounds further comprise at least one fluorine-containing group selected from the group consisting of perfluoroalkyl, perfluoroheteroalkyl, and perfluoroheteroalkylene. The ester oligomers may further comprises one or more non-fluorinated polyols.

Optionally the compounds may further comprise one or more water-solubilizing groups by the further reaction product of a compound comprising one or more water solubilizing groups selected from the group consisting of carboxylate, sulfate, sulfonate, phosphate, phosphonate, ammonium, and quaternary ammonium groups, and at least one electrophilic or nucleophilic moiety reactive with a hydroxyl group or an acyl group.

Optionally the compounds may further comprise one or more polymerizable groups by the further reaction product of a compound comprising one or more polymerizable groups and at least one electrophilic or nucleophilic moiety reactive with a hydroxyl group or an acyl group.

The compound or oligomer comprises at least one repeatable or repeating polymerized unit. Each repeatable or repeating unit comprises one or more pendant or in-chain fluorine-containing groups selected from the group consisting of perfluoroalkyl, perfluoroalkylene, perfluoroheteroalkyl, and perfluoroheteroalkylene, and an ester group that is formed from the reaction between a polyol and a polyacyl compound. The compound or oligomer is terminated with (i) one or more perfluoroalkyl groups, one or more perfluoroheteroalkyl groups, or a mixture thereof. For brevity "oligomer" shall be inclusive of compounds and oligomers.

In one preferred embodiment, the fluorochemical composition of the present invention comprises a mixture of ester molecules arising from the reaction of (a) one or more polyacyl compounds, (b) one or more polyols, and (c) one or more fluorochemical monofunctional compounds, wherein at least one of said polyols compounds comprises a fluorinated group. The mixture of ester molecules preferably comprises ester molecules having a varying number of repeating or repeatable units, including zero, one, two, and more repeating units. This mixture of ester molecules comprising a varying number of repeating units allows simple blending of the above components in preparing the fluorochemical composition.

The fluorochemical composition of the present invention comprises a mixture of ester molecules arising from the reaction of at least one diacyl compound (or a derivative thereof, for example, a dicarboxylic acid halide, a dicarboxylic acid anhydride, or a dicarboxylic acid ester), at least one fluorinated polyol, and at least one fluorine-containing monoalcohol or fluorine-containing monocarboxylic acid (or derivative), with the proviso that at least a portion of the polyol compounds is comprised of a pendant or in-chain fluorine-containing group.

Thus, the fluorochemical composition can comprise a single fluorine-containing ester compound or oligomer having a certain number of the specified repeating or repeatable units (a number greater than or equal to one), or it can comprise a mixture of such compounds and/or oligomers of varying numbers of repeat units. Preferably, the composition comprises a mixture of ester molecules of varying structure, more preferably, a mixture of at least one ester oligomer (2 or more repeat units) and at least one ester compound (1 repeatable unit). The overall fluorochemical composition generally contains, relative to the amount of solids present in the system, at least about 3 weight percent, preferably at least about 5 weight percent, carbon-bound fluorine in the form of fluorochemical groups.

The ester compounds and oligomers may be represented by the following formula (I):

$$R_fQ[OR^2]_o[-OC(O)-R^1-C(O)O-R^2O-]_n[C(O)-R^1-C(O)]_m-Z \quad (I)$$

wherein:

o is a number from 0 to 1 inclusive;

n is a number from 1 to 10 inclusive;

m is is number from 0 to 1 inclusive;

$R_f$ is a perfluoroalkyl group having 1 to 12, preferably 6 or fewer, most preferably 3 to 5 carbon atoms, or a perfluoroheteroalkyl group having 3 to about 50 carbon atoms with all perfluorocarbon chains present having 1 to 6, preferably 1 to 4 carbon atoms;

Q is a divalent linking group;

$R^1$ is a polyvalent organic groups that is a residue of a polyacyl compound, that is a straight or branched chain alkylene, cycloalkylene, or heteroalkylene group of 1 to 14 carbon atoms, preferably 1 to 8 carbon atoms, more preferably 1 to 4 carbon atoms, and most preferably two carbon atoms; or an arylene of 6 to 12 carbon atoms;

$R^2$ is a divalent organic group that is a residue of the polyol, at least a portion of which are substituted with or contain one or more perfluoroalkyl groups, perfluoroheteroalkyl groups, perfluoroheteroalkylene groups, or mixtures thereof; and Z is $R_fQ-$, a water-solubilizing group, or a polymerizable group.

With respect to the above-described $R_f$ groups, it is preferred that the $R_f$ group have 6 or fewer carbon atoms. It is believed that the shorter-chain $R_f$ groups have a reduced tendency to bioaccumulate as described in U.S. Pat. No. 5,688,884.

With respect to the above-described $R^1$ groups, it will be understood that the $R^1$ group may further be substituted with a pendant acyl group (or equivalent thereof), as would be the case if the polyacyl compound were a triacyl compound such as a triester. The "third" acyl group, pendant from $R^1$, may serve as a point of attachment of a polymerizable compound, or a water-solubilizing compound. Similarly, the $R^2$ groups may be further substituted with pendent hydroxy groups, as would be the case if the polyol were a triol. The "third" hydroxy group, pendant from $R^2$, may also serve as a point of attachment of a polymerizable compound, or a water-solubilizing compound.

Suitable linking groups Q include the following structures in addition to a covalent bond. For the purposes of this list, each k is independently an integer from 0 to about 20, $R_1'$ is hydrogen, phenyl, or alkyl of 1 to about 4 carbon atoms, and $R_2'$ is alkyl of 1 to about 20 carbon atoms. Each structure is non-directional, i.e. $-(CH_2)_kC(O)O-$ is equivalent to $-O(O)C(CH_2)_k-$.

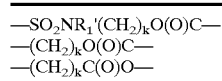
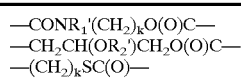

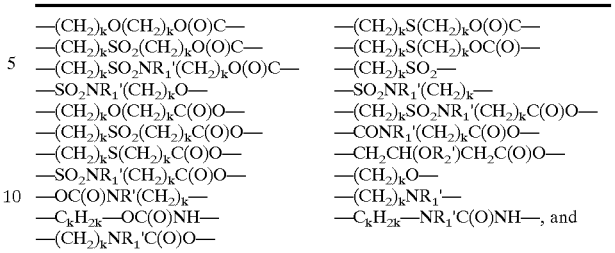

It will be understood that mixtures of compounds corresponding to the general formula may be represented, in addition to single compounds, and that o, m and n may be represented by non-integral values.

Preferred classes of fluorine-containing ester compounds and oligomers are those represented by the following formulas $$R_fZR^1-O-(C=O)-R^3-(C=O)-O-[R^4-O-(C=O)-R^3-(C=O)-O]_n-R^1ZR_f \quad \text{formula (IV)}$$

$$R_fZR^1-(C=O)-O-R^4-O-(C=O)-[R^3-(C=O)-O-R^4-O-(C=O)]_n-R^1ZR_f \quad \text{formula (V)}$$

(with those of Formulas IV being more preferred) wherein each $R^1ZR_f$ is independently the residue of at least one fluorine-containing monoalcohol or fluorine-containing monocarboxylic acid (or derivative); each $R^3$ and each $R^4$ independently comprises at least one aliphatic, heteroaliphatic, saturated alicyclic, saturated heteroalicyclic, aromatic, heteroaromatic, or polymeric moiety; and n is an integer of at least one; with the proviso that $R^4$ comprises a pendant or in-chain fluorine-containing group. The aromatic or heteroaromatic moiety can comprise one or more rings (which can be fused or can be separated by one or more spacer groups, for example, an aliphatic group), and the adjacent ester groups can be bonded to a single ring or to separate rings of the aromatic or heteroaromatic moiety. The rings can be substituted with other groups that do not interfere with the reactivity of carboxylic acid or hydroxyl groups, do not cause undesirable side reactions, and do not cause decomposition of the resulting fluorochemical composition during use (for example, one or more halogen, alkyl, alkoxy, or aryl groups substituted for one or more ring-bonded hydrogen atoms). The polymeric moiety preferably has a number average molecular weight in the range of about 500 to about 4000 (more preferably, about 1000 to about 2500).

$R_f$, Z, and $R^1$ are as described. When a fluorine-containing monocarboxylic acid (or derivative) is used, Z and $R^1$ taken together can be a covalent bond. When $R^3$ is aromatic, $R^3$ is preferably phenylene, napthalene, biphenylene, bis(phenylene)methylene, or bis(phenylene)propylidene (more preferably, phenylene; most preferably, meta- or para-phenylene). When $R^4$ is not comprised of a fluorine-containing group it is preferably a divalent aliphatic, saturated alicyclic, aliphatic polyester, or poly(oxyalkylene) moiety; more preferably, a divalent aliphatic, aliphatic polyester, or poly(oxyalkylene) moiety; even more preferably, hexylene, ethylene, propylene, butylene, neopentylene, ethyleneoxyethylene, bis(ethyleneoxycarbonyl)phenylene, polycaprolactone, polyoxyethylene, or polyoxypropylene; most preferably, hexylene, butylene, ethylene, or propylene. n is generally an integer in the range of 1 to about 10; preferably, 1 to 8; more preferably, 1 to 6; most preferably, 1 to 4.

Polyols, suitable for use in preparing the fluorochemical compositions of the present invention comprising a mixture of polyol molecules, include those organic polyols that have an average hydroxyl functionality of greater than 1 (preferably about 2 to 3; most preferably, about 2, as diols are most preferred). The hydroxyl groups can be primary or secondary, with primary hydroxyl groups being preferred for their greater reactivity.

Suitable polyols include those that comprise at least one aliphatic, heteroaliphatic, alicyclic, heteroalicyclic, aromatic, heteroaromatic, or polymeric moiety. Preferred polyols are aliphatic or polymeric polyols that contain hydroxyl groups as terminal groups.

The polyols may comprise at least one fluorine-containing group selected from the group consisting of perfluoroalkyl, perfluoroheteroalkyl, and perfluoroalkylene moieties. All of the perfluorocarbon chains, comprising these perfluoro moieties, are preferably six or fewer carbon atoms. Perfluoroalkyl moieties are preferred, with perfluoroalkyl moieties having 6 or fewer carbon atoms being preferred and 3 to 5 carbon atoms being most preferred. Perfluoroheteroalkyl moieties may have 3 to 50 carbon atoms. Perfluoroheteroalkylene groups may have from about 3 to about 50 carbon atoms. Perfluoroheteroalkyl and alkylene moieties are preferably perfluoropolyethers with no perfluorocarbon chain of more than six carbon atoms.

Mixtures of fluorinated and non-fluorinated polyols may be advantageously utilized in preparing certain of the fluorochemical compositions of the instant invention. For example, inclusion of a non-fluorinated polyol can alter the melt temperature of the fluorochemical composition, making it more effective at the processing temperatures normally used in a given application. Increased cost effectiveness is also achieved by replacing a portion of the more expensive fluorinated polyol(s) with the less expensive non-fluorinated polyol(s). The selection of the non-fluorinated polyol(s) and the amount to use is determined by the performance requirements, for example melt temperature and repellency. A useful range of ratios of non-fluorinated polyol(s) to fluorinated polyols is about 1:1 to about 1:100.

Thus, the fluorochemical ester oligomer may comprise the condensation reaction products of one or more fluorinated polyols, one or more non-fluorinated polyols, one or more polyacyl compounds and one or more monofunctional fluorine-containing compounds.

Polyols useful in the present invention may optionally be substituted with or contain other groups, including water-solubilizing groups and polymerizable groups. Solubilizing groups include carboxylate, sulfate, sulfonate, phosphate, phosphonate, ammonium, quaternary ammonium, and the like. Polymerizable groups include acrylate, methacrylate, vinyl, allyl, glycidyl, and the like. Both the fluorinated and non-fluorinated polyols may further comprise a water-solubilizing or polymerizable groups.

Representative examples of suitable fluorinated polyols comprised of at least one fluorine-containing group include $R_fSO_2N(CH_2CH_2OH)_2$ such as N-bis(2-hydroxyethyl) perfluorobutylsulfonamide; $R_fOC_6H_4SO_2N(CH_2CH_2OH)_2$; $R_fSO_2N(R')CH_2CH(OH)CH_2OH$ such as $C_6F_{13}SO_2N(C_3H_7)CH_2CH(OH)CH_2OH$; $R_fCH_2CON(CH_2CH_2OH)_2$; $R_fCON(CH_2CH_2OH)_2$; $CF_3CF_2(OCF_2CF_2)_3OCF_2CON(CH3)CH2CH(OH)CH2OH$; $R_fOCH_2CH(OH)CH_2OH$ such as $C_4F_9OCH_2CH(OH)CH_2OH$; $R_fCH_2CH_2SC_3H_6OCH_2CH(OH)CH_2OH$; $R_fCH_2CH_2SC_3H_6CH(CH_2OH)_2$; $R_fCH_2CH_2SCH_2CH(OH)CH_2OH$; $R_fCH_2CH_2SCH(CH_2OH)CH_2CH_2OH$; $R_fCH_2CH_2SCH_2CH(OH)CH_2OH$ such as $C_5F_{11}(CH_2)_3SCH_2CH(OH)CH_2OH$; $R_fCH_2CH_2CH_2OCH_2CH(OH)CH_2OH$ such as $C_5F_{11}(CH_2)_3OCH_2CH(OH)CH_2OH$; $R_fCH_2CH_2CH_2OC_2H_4OCH_2CH(OH)CH_2OH$; $R_fCH_2CH_2(CH_3)OCH_2CH(OH)CH_2OH$; $R_f(CH_2)_4SC_3H_6CH(CH_2OH)CH_2OH$; $R_f(CH_2)_4SCH_2CH(CH_2OH)_2$; $R_f(CH_2)_4SC_3H_6OCH_2CH(OH)CH_2OH$; $R_fCH_2CH(C_4H_9)SCH_2CH(OH)CH_2OH$; $R_fCH_2OCH_2CH(OH)CH_2OH$; $R_fCH2CH(OH)CH_2SCH_2CH_2OH$; $R_fCH_2CH(OH)CH_2SCH_2CH_2OH$; $R_fCH_2CH(OH)CH_2OCH_2CH_2OH$; $R_fCH_2CH(OH)CH_2OH$; $R_fR''SCH(R'''OH)CH(R'''OH)SR''R_f$; $(R_fCH_2CH_2SCH_2CH_2SCH_2)_2C(CH_2OH)_2$; $((CF_3)_2CFO(CF_2)_2(CH_2)_2SCH_2)_2C(CH_2OH)_2$; $(R_fR''SCH_2)_2C(CH_2OH)_2$; 1,4-bis(1-hydroxy-1,1-dihydroperfluoroethoxyethoxy)perfluoro-n-butane $(HOCH_2CF_2OC_2F_4O(CF_2)_4OC_2F_4OCF_2CH_2OH)$; 1,4-bis(1-hydroxy-1,1-dihydroperfluoropropoxy)perfluoro-n-butane $(HOCH_2CF_2CF_2O(CF_2)_4OCF_2CF_2CH_2OH)$; fluorinated oxetane polyols made by the ring-opening polymerization of fluorinated oxetane such as Poly-3-Fox™ (available from Omnova Solutions, Inc., Akron Ohio); polyetheralcohols prepared by ring opening addition polymerization of a fluorinated organic group substituted epoxide with a compound containing at least two hydroxyl groups as described in U.S. Pat. No. 4,508,916 (Newell et al); and perfluoropolyether diols such as Fomblin™ ZDOL $(HOCH_2CF_2O(CF_2O)_{8-12}(CF_2CF_2O)_{8-12}CF_2CH_2OH$, available from Ausimont); wherein $R_f$ is a perfluoroalkyl group having 1 to 6 carbon atoms, or a perfluoroheteroalkyl group having 3 to about 50 carbon atoms with all perfluorocarbon chains present having 6 or fewer carbon atoms, or mixtures thereof; R' is alkyl of 1 to 4 carbon atoms; R'' is branched or straight cahin alkylene of 1 to 12 carbon atoms, alkylenethio-alkylene of 2 to 12 carbon atoms, alkyleneoxyalkylene of 2 to 12 carbon atoms, or alkylene iminoalkylene of 2 to 12 carbon atoms, where the nitrogen atom contains as a third substituent hydrogen or alkyl of 1 to 6 carbon atoms; and R''' is a straight or branched chain alkylene of 1 to 12 carbon atoms or an alkylene-polyoxyalkylene of formula $C_rH_{2r}(OC_sH_{2s})n$ where r is 1–12, s is 2–6, and t is 1–40.

Preferred polyols comprised of at least one fluorine-containing group include N-bis(2-hydroxyethyl) perfluorobutylsulfonamide; fluorinated oxetane polyols made by the ring-opening polymerization of fluorinated oxetane such as Poly-3-Fox™ (available from Omnova Solutions, Inc., Akron Ohio); polyetheralcohols prepared by ring opening addition polymerization of a fluorinated organic group substituted epoxide with a compound containing at least two hydroxyl groups as described in U.S. Pat. No. 4,508,916 (Newell et al); perfluoropolyether diols such as Fomblin™ ZDOL $(HOCH_2CF_2O(CF_2O)_{8-12}(CF_2CF_2O)_{8-12}CF_2CH_2OH$, available from Ausimont); 1,4-bis(1-hydroxy-1,1-dihydroperfluoroethoxyethoxy)perfluoro-n-butane $(HOCH_2CF_2OC_2F_4O(CF_2)_4OC_2F_4OCF_2CH_2OH)$; and 1,4-bis(1-hydroxy-1,1-dihydroperfluoropropoxy) perfluoro-n-butane $(HOCH_2CF_2CF_2O(CF_2)_4OCF_2CF_2CH_2OH)$.

More preferred polyols comprised of at least one fluorine-containing group include N-bis(2-hydroxyethyl) perfluorobutylsulfonamide; 1,4-bis(1-hydroxy-1,1-dihydroperfluoropropoxy)perfluoro-n-butane $(HOCH_2CF_2CF_2O(CF_2)_4OCF_2CF_2CH_2OH)$.

Representative examples of suitable non-polymeric, non-fluorinated polyols include alkylene glycols, polyhydroxyalkanes, and other polyhydroxy compounds. The alkylene glycols include, for example, 1,2-ethanediol; 1,2-propanediol; 3-chloro-1,2-propanediol; 1,3-propanediol; 1,3-butanediol; 1,4-butanediol; 2-methyl-1,3- propanediol; 2,2-dimethyl-1,3-propanediol (neopentylglycol); 2-ethyl-1,3-propanediol; 2,2-diethyl-1,3-propanediol; 1,5-pentanediol; 2-ethyl-1,3-pentanediol; 2,2,4-trimethyl-1,3-pentanediol; 3-methyl-1,5-pentanediol; 1,2-, 1,5-, and 1,6-hexanediol; 2-ethyl-1,6-hexanediol; bis(hydroxymethyl)cyclohexane; 1,8-octanediol; bicyclo-octanediol; 1,10-decanediol; tricyclo-decanediol; norbornanediol; and 1,18-dihydroxyoctadecane. The polyhydroxyalkanes include, for example, glycerine; trimethylolethane; trimethylolpropane; 2-ethyl-2-(hydroxymethyl)-1,3-propanediol; 1,2,6-hexanetriol; pentaerythritol; quinitol; mannitol; and sorbitol. The other polyhydroxy compounds include, for example, polyols such as di(ethylene glycol); tri(ethylene glycol); tetra(ethylene glycol); tetramethylene glycol; dipropylene glycol; diisopropylene glycol; tripropylene glycol; bis(hydroxymethyl) propionic acid; N,N-bis(2-hydroxyethyl)-3-aminopropyltriethoxysilane; bicine; 1,11-(3,6-dioxaundecane)diol; 1,14-(3,6,9,12-tetraoxatetradecane)diol; 1,8-(3,6-dioxa-2,5,8-trimethyloctane)diol; 1,14-(5,10-dioxatetradecane)diol; castor oil; 2-butyne-1,4-diol; N,N-bis(hydroxyethyl)benzamide; 4,4'-bis(hydroxymethyl) diphenylsulfone; 1,4-benzenedimethanol; 1,3-bis(2-hydroxyethyoxy)benzene; 1,2-dihydroxybenzene; resorcinol; 1,4-dihydroxybenzene; 3,5-, 2,6-, 2,5-, and 2,4-dihydroxybenzoic acid; 1,6-, 2,6-, 2,5-, and 2,7-dihydroxynaphthalene; 2,2'- and 4,4'-biphenol; 1,8-dihydroxybiphenyl; 2,4-dihydroxy-6-methyl-pyrimidine; 4,6-dihydroxypyrimidine; 3,6-dihydroxypyridazine; bisphenol A; 4,4'-ethylidenebisphenol; 4,4'-isopropylidenebis(2,6-dimethylphenol); bis(4-hydroxyphenyl)methane; 1,1-bis(4-hydroxyphenyl)-1-phenylethane (bisphenol C); 1,4-bis(2-hydroxyethyl)piperazine; bis(4-hydroxyphenyl) ether; as well as other aliphatic, heteroaliphatic, saturated alicyclic, aromatic, saturated heteroalicyclic, and heteroaromatic polyols; and the like, and mixtures thereof.

Representative examples of useful polymeric non-fluorinated polyols include polyoxyethylene, polyoxypropylene, and ethylene oxide-terminated polypropylene glycols and triols of molecular weights from about 200 to about 2000, corresponding to equivalent weights of about 100 to about 1000 for the diols or about 70 to about 700 for triols; polytetramethylene glycols of varying molecular weight; polydialkylsiloxane diols of varying molecular weight; hydroxy-terminated polyesters and hydroxy-terminated polylactones (e.g., polycaprolactone polyols); hydroxy-terminated polyalkadienes (e.g., hydroxyl-terminated polybutadienes); and the like. Mixtures of polymeric polyols can be used if desired.

Useful commercially available polymeric non-fluorinated polyols include Carbowax™ poly(ethylene glycol) materials in the number average molecular weight ($M_n$) range of from about 200 to about 2000 (available from Union Carbide Corp.); poly(propylene glycol) materials such as PPG-425 (available from Lyondell Chemicals); block copolymers of poly(ethylene glycol) and poly(propylene glycol) such as Pluronic™ L31 (available from BASF Corporation); Bisphenol A ethoxylate, Bisphenol A propyloxylate, and Bisphenol A propoxylate/ethoxylate (available from Sigma-Aldrich); polytetramethylene ether glycols such as Polymeg™ 650 and 1000 (available from Quaker Oats Company) and the Terathane™ polyols (available from DuPont); hydroxyl-terminated polybutadiene resins such as the Poly bd™ materials (available from Elf Atochem); the "PeP" series (available from Wyandotte Chemicals Corporation) of polyoxyalkylene tetrols having secondary hydroxyl groups, for example, "PeP" 450, 550, and 650; polycaprolactone polyols with $M_n$ in the range of about 200 to about 2000 such as Tone™ 0201, 0210, 0301, and 0310 (available from Union Carbide); "Paraplex™ U-148" (available from Rohm and Haas), an aliphatic polyester diol; polyester polyols such as the Multron™ poly(ethyleneadipate)polyols (available from Mobay Chemical Co.); polycarbonate diols such as Duracarb™ 120, a hexanediol carbonate with $M_n$=900 (available from PPG Industries Inc.); and the like; and mixtures thereof.

Preferred non-fluorinated polyols include 1,2-ethanediol; 1,2- and 1,3-propanediol; 1,3- and 1,4-butanediol; neopentylglycol; 1,5-pentanediol; 3-methyl-1,5-pentanediol; 1,2-, 1,5-, and 1,6-hexanediol; bis(hydroxymethyl)cyclohexane; 1,8-octanediol; 1,10-decanediol; di(ethylene glycol); tri(ethylene glycol); tetra(ethylene glycol); di(propylene glycol); di(isopropylene glycol); tri(propylene glycol); poly(ethylene glycol) diols (number average molecular weight of about 200 to about 1500); poly(di(ethylene glycol) phthalate) diol (having number average molecular weights of, for example, about 350 or about 575); poly(propylene glycols) diols (number average molecular weight of about 200 to about 500); block copolymers of poly(ethylene glycol) and poly(propylene glycol) such as Pluronic™ L31 (available from BASF Corporation); polycaprolactone diols (number average molecular weight of about 200 to about 600); resorcinol; hydroquinone; 1,6-, 2,5-, 2,6-, and 2,7-dihydroxynaphthalene; 4,4'-biphenol; bisphenol A; bis(4-hydroxyphenyl)methane; and the like; and mixtures thereof.

More preferred non-fluorinated polyols include 1,2-ethanediol; 1,2- and 1,3-propanediol; 1,4-butanediol; neopentylglycol; 1,2- and 1,6-hexanediol; di(ethylene glycol); tri(ethylene glycol); poly(di(ethylene glycol) phthalate) diol (having number average molecular weights of, for example, about 350 or about 575); poly(ethylene glycol) diols (having number average molecular weights of, for example, about 200, 300, 400); polypropylene glycol (having a number average molecular weight of, for example, about 425); dimer diol; polycaprolactone diol (having a number average molecular weight of, for example, about 530); 3,5-dihydroxybenzene; bisphenol A; resorcinol; hydroquinone; and mixtures thereof.

Polyacyl compounds and derivatives thereof (for example, dicarboxylic acid halides, dicarboxylic acid anhydrides, and dicarboxylic acid esters) suitable for use in preparing the fluorochemical composition comprise at least one aliphatic, heteroaliphatic (that is, containing in-chain heteroatoms, such as nitrogen, oxygen, or sulfur), saturated alicyclic, saturated heteroalicyclic, or polymeric moiety. The polyacyl compounds can optionally contain one or more "non-interfering" groups (groups that do not interfere with the reactivity of the acyl groups, do not cause undesirable side reactions, and do not cause decomposition of the resulting fluorochemical composition), for example, alkyl, sulfonate, ester, ether, halo, haloalkyl, amide, or carbamate groups. Preferably, the polyacyl compounds are aliphatic in nature.

Acyl derivatives are sometimes preferred over acids for a variety of reasons. For example, acyl halides provide both relatively fast reaction rates and reactions that tend to go to completion. The resulting HCl is volatile and can be removed under vacuum or by other removal means, such as by water washing.

For applications in which evolution of HCl is undesirable, a lower alkyl acyl ester can be used. Use of such lower alkyl esters can facilitate processing, due to their lower melting points and greater solubility in some solvents (relative to the corresponding acids). Continuous removal of the resulting lower alkyl alcohol can be employed to bring the reaction to completion. A catalyst, such as p-toluenesulfonic acid or trifluoromethanesulfonic acid, can also be used and can be selected so as to be removable or deactivatable (e.g. reacted with CaO) after reaction is complete, or so as to cause minimal decomposition of the resulting fluorochemical composition under use conditions.

Anhydrides can also be used. Particularly useful anhydride derivatives of dicarboxylic acids are cyclic anhydrides, which react relatively rapidly with an alcohol to form an ester and a carboxylic acid group. This allows a preponderance of monoester/monocarboxylic acid to be formed from the reaction of the cyclic anhydride with one alcohol (such as the fluorine-containing monoalcohol), followed by reaction of the remaining carboxylic acid groups with a second alcohol (such as the polyol). Alternatively, the remaining carboxylic acid groups can first be converted to the corresponding acid halide and then reacted with the second alcohol.

Representative examples of suitable dicarboxylic acids and dicarboxylic acid derivatives include the following acids and their corresponding esters, halides, and anhydrides: azelaic; maleic; fumaric; itaconic; 1,5-pent-2-enedioic; adipic; 2-methyleneadipic; 3-methylitaconic; 3,3-dimethylitaconic; sebacic; suberic; pimelic; succinic; benzylsuccinic; sulfosuccinic; gluratic; 2-methyleneglutaric; 2-sulfoglutaric; 3-sulfoglutaric; diglycolic; dilactic; 3,3'-(ethylenedioxy)dipropionic; dodecanedioic; 2-sulfododecanedioic; decanedioic; undecanedicarboxylic; hexadecanedicarboxylic; dimerized fatty acids (such as those obtained by the dimerization of olefinically unsaturated monocarboxylic acids containing 16 to 20 carbon atoms, for example, oleic acid and linoleic acid and the like); 1,2-, 1,4-, and 1,6-cyclohexanedicarboxylic; norbornenedicarboxylic; bi-cyclooctanedicarboxylic; and other aliphatic, heteroaliphatic, saturated alicyclic, or saturated heteroalicyclic dicarboxylic acids; and the like; and mixtures thereof. Salts (for example, alkali metal salts) of the above-described sulfonic acids can also be used.

Preferred dicarboxylic acids and dicarboxylic acid derivatives include succinic, adipic, dimer acid, azelaic acid, dodecanedioic acid, poly(ethylene glycol) diacid, citric acid, poly(acrylic acid), pimelic, suberic, and sebacic acids (and derivatives thereof), and the like, and mixtures thereof; with suberic, and adipic acids (and derivatives thereof), and mixtures thereof being more preferred.

When fluorochemical compositions of the present invention are used as topical treatments, aliphatic dicarboxylic acids (and derivatives thereof) are preferred.

Fluorochemical monofunctional compounds, useful in preparing the fluorochemical compositions of the present invention comprising a mixture of ester molecules, include those that comprise at least one $R_f$ group. The $R_f$ groups can contain straight chain, branched chain, or cyclic fluorinated alkylene groups or any combination thereof. The $R_f$ groups can optionally contain one or more heteroatoms (i.e. oxygen, sulfur, and/or nitrogen) in the carbon-carbon chain so as to form a carbon-heteroatom-carbon chain (i.e. a heteroalkylene group). Fully-fluorinated groups are generally preferred, but hydrogen or chlorine atoms can also be present as substituents, provided that no more than one atom of either is present for every two carbon atoms. It is additionally preferred that any $R_f$ group contain at least about 40% fluorine by weight, more preferably at least about 50% fluorine by weight. The terminal portion of the group is generally fully-fluorinated, preferably containing at least three fluorine atoms, e.g., $CF_3O-$, $CF_3CF_2-$, $CF_3CF_2CF_2-$, $(CF_3)_2N-$, $(CF_3)_2CF-$, $SF_5CF_2-$. Perfluorinated aliphatic groups (i.e., those of the formula $C_nF_{2n+1}-$) wherein n is 1 to 12 inclusive are the preferred $R_f$ groups, with n=6 or fewer being more preferred and with n=3 to 5 being the most preferred. Further, it is preferred that the fluorochemical monofunctional compounds have a melting point above room temperature. It has been found that the oligomers derived from solid fluorochemical monofunctional compounds exhibit higher contact angle performance than lower melting compounds.

Useful fluorine-containing monofunctional compounds include compounds of the following formula III:

formula (II)

wherein:

$R_f$ is a a perfluoroalkyl group having 1 to 12 carbon atoms, or a perfluoroheteroalkyl group having 3 to about 50 carbon atoms with all perfluorocarbon chains present having 6 or fewer carbon atoms;

Q' is a moiety comprising a functional group that is reactive toward the terminal acyl (of the polyacyl compound) or hydroxyl groups (of the polyol).

It will be understood with reference to Formula I that the compound $R_fQ'$ reacts with the polyol or acyl compounds to provide the terminal moiety $R_fQ-$ $R_fQ'$ may comprise fluorine-containing monoalcohols including the following:

| | |
|---|---|
| $R_fSO_2N(CH_3)CH_2CH_2OH$, | $CF_3(CF_2)_3SO_2N(CH_3)CH_2CH_2OH$, |
| $CF_3(CF_2)_3SO_2N(CH_3)CH(CH_3)CH_2OH$, | $CF_3(CF_2)_3SO_2N(CH_3)CH_2CH(CH_3)OH$, |
| | $R_fSO_2N(H)(CH_2)_2OH$, |
| $R_fSO_2N(CH_3)(CH_2)_4OH$, | $C_4F_9SO_2N(CH_3)(CH_2)_4OH$ |
| $C_6F_{13}SO_2N(CH_3)(CH_2)_4OH$, | $R_fSO_2N(CH_3)(CH_2)_{11}OH$, |
| $R_fSO_2N(C_2H_5)CH_2CH_2OH$, | $CF_3(CF_2)_3SO_2N(C_2H_5)CH_2CH_2OH$, |
| $C_6F_{13}SO_2N(C_2H_5)CH_2CH_2OH$ | $R_fSO_2N(C_2H_5)(CH_2)_6OH$, |
| $R_fSO_2N(C_2H_5)(CH_2)_{11}OH$, | $R_fSO_2N(C_3H_7)CH_2OCH_2CH_2OH$, |
| $R_fSO_2N(CH_2CH_2CH_3)CH_2CH_2OH$, | $R_fSO_2N(C_4H_9)(CH_2)_4OH$, |
| $R_fSO_2N(C_4H_9)CH_2CH_2OH$, | $C_3F_7CONHCH_2CH_2OH$, |
| 2-(N-methyl-2-(4-perfluoro-(2,6-diethylmorpholinyl))perfluoroethylsulfonamido)ethanol, | |
| $R_fCON(CH_3)CH_2CH_2OH$, | $R_fCON(C_2H_5)CH_2CH_2OH$, |
| $R_fCON(CH_3)(CH_2)_{11}OH$, | $R_fCON(H)CH_2CH_2OH$ |
| $C_2F_5O(C_2F_4O)_3CF_2CONHC_2H_4OH$, | $CF_3O(CF(CF_3)CF_2O)_{1-36}CF(CF_3)CH_2OH$, |
| $C_2F_5O(CF(CF_3)CF_2O)_{1-36}CF(CF_3)CH_2OH$, | $C_3F_7O(CF(CF_3)CF_2O)_{1-36}CF(CF_3)CH_2OH$, |
| $C_4F_9O(CF(CF_3)CF_2O)_{1-36}CF(CF_3)CH_2OH$, | $C_3F_7O(CF(CF_3)CF_2O)_{12}CF(CF_3)CH_2OH$, |
| $CF_3O(CF_2CF_2O)_{1-36}CF_2CH_2OH$, | $C_2F_5O(CF_2CF_2O)_{1-36}CF_2CH_2OH$, |

-continued

| | |
|---|---|
| $C_3F_7O(CF_2CF_2O)_{1-36}CF_2CH_2OH$, | $C_4F_9O(CF_2CF_2O)_{1-36}CF_2CH_2OH$, |
| n-$C_4F_9OC_2F_4OCF_2CH_2OCH_2CH_2OH$ | $CF_3O(CF_2CF_2O)_{11}CF_2CH_2OH$, |
| $R_fSO_2CH_2CH_2OH$, | $R_fCOOCH_2CH_2CH(CH_3)OH$ |
| $R_fCOOCH_2CH_2OH$, | $C_5F_{11}COOCH_2CH_2OH$, |
| $R_f(CH_2)_{11}N(C_2H_5)CH_2CH_2OH$, | $R_fCH_2OH$, |
| $C_3F_7CH_2OH$, | Perfluoro(cyclohexyl)methanol |
| $C_4F_9CH_2CH_2OH$, | $CF_3(CF_2)_5CH_2CH_2OH$ |
| $R_fCH_2CH_2SO_2N(CH_3)CH_2CH_2OH$, | $CF_3(CF_2)_5CH_2CH_2SO_2N(CH_3)CH_2CH_2OH$, |
| $CF_3(CF_2)_3CH_2CH_2SO_2N(CH_3)CH_2CH_2OH$, | $R_fCH_2CH_2CH_2OH$, |
| $R_f(CH_2)_2OH$, | $R_f(CH_2)_2S(CH_2)_2OH$, |
| $C_4F_9(CH_2)_2S(CH_2)_2OH$, | $R_f(CH_2)_4S(CH_2)_2OH$, |
| $R_f(CH_2)_2S(CH_2)_3OH$, | $R_f(CH_2)_2SCH(CH_3)CH_2OH$, |
| $R_f(CH_2)_4SCH(CH_3)CH_2OH$, | $R_fCH_2CH(CH_3)S(CH_2)_2OH$, |
| $R_f(CH_2)_2S(CH_2)_{11}OH$, | $R_f(CH_2)_2S(CH_2)_3O(CH_2)_2OH$, |
| $R_f(CH_2)_3O(CH_2)_2OH$, | $R_f(CH_2)_3SCH(CH_3)CH_2OH$, and |
| $R_fSO_2N(H)(C_2H_4)O—C(O)(CH_2)_5—OH$ | | and the like, and mixtures thereof, wherein $R_f$ is a a perfluoroalkyl group having 1 to 12 carbon atoms, or a perfluoroheteroalkyl group having 3 to about 50 carbon atoms with all perfluorocarbon chains present having 6 or fewer carbon atoms. If desired, rather than using such alcohols, similar thiols can be utilized.

Preferred fluorine-containing monoalcohols include 2-(N-methylperfluorobutanesulfonamido)ethanol; 2-(N-ethylperfluorobutanesulfonamido) ethanol; 2-(N-methylperfluorobutanesulfonamido)propanol; N-methyl-N-(4-hydroxybutyl)perfluorohexanesulfonamide; 1,1,2,2-tetrahydroperfluorooctanol; 1,1-dihydroperfluorooctanol; $C_6F_{13}CF(CF_3)CO_2C_2H_4CH(CH_3)OH$; n-$C_6F_{13}CF(CF_3)CON(H)CH_2CH_2OH$; $C_4F_9OC_2F_4OCF_2CH_2OCH_2CH_2OH$; $C_3F_7CON(H)CH_2CH_2OH$; 1,1,2,2,3,3-hexahydroperfluorodecanol; $C_3F_7O(CF(CF_3)CF_2O)_{1-36}CF(CF_3)CH_2OH$; $CF_3O(CF_2CF_2O)_{1-36}CF_2CH_2OH$; $C_4F_9—SO_2NMeC_2H_4OH$, and the like; and mixtures thereof.

The fluorochemical monofunctional compound, $R_fQ'$, may comprise derivatives (such as esters or acid halides) of fluorine-containing monocarboxylic acids including (1) those having the formula $R_f(CH_2)_n(X)_p(CH_2)_mCOOH$, wherein $R_f$ is as defined above, n and m are independently integers of 0 to 14 (preferably 0–8, more preferably 0–4), X is divalent oxygen or sulfur, and p is an integer of 0 or 1, and (2) those having the formula $R_fQR'COOH$, wherein $R_f$ is as defined above, R' is a divalent alkyl (straight chain or branched) or cycloalkyl radical having from 1 to about 12 carbon atoms (preferably from 1 to about 8 carbon atoms, more preferably from 1 to about 4 carbon atoms), and the divalent linking group Q is —$SO_2N(R")$— or —$CON(R")$— wherein R" is a monovalent alkyl (straight chain or branched), cycloalkyl, or aryl radical having from 1 to about 12 carbon atoms (preferably from 1 to about 8 carbon atoms, more preferably from 1 to about 4 carbon atoms).

Representative examples of useful derivatives of fluorine-containing monocarboxylic acids include perfluorobutanoic ($C_3F_7COOH$), perfluoroisobutanoic (($CF_3$)$_2$CFCOOH), hydroperfluorobutanoic ($C_3F_6HCOOH$), perfluoropentanoic ($C_4F_9COOH$), hydroperfluoropentanoic ($C_4F_8HCOOH$), perfluorohexanoic ($C_5F_{11}COOH$), hydroperfluorohexanoic ($C_5F_{10}HCOOH$), perfluorcyclohexanyl carboxylic ($C_6F_{11}COOH$), perfluoroheptanoic ($C_6F_{13}COOH$), perfluoro(3-ethoxypropionic), perfluoro(3-propoxypropionic), perfluoro(3-butoxypropionic), perfluoro(3-pentoxypropionic), $R_f[OCF(CF_3)CF_2]_{1-6}OCF(CF_3)COOH$ where $R_f$ is a perfluroalkyl group of 1–12 carbon atoms, 4-(4-perfluoroisopropoxyperfluorobutyl) butanoic, 4-(bis(perfluoroisopropyl)fluoromethoxy) perfluorobutanoic, 12-(2-perfluoroisopropoxyperfluoroethyl)dodecanoic, 6-(2-perfluorocyclobutoxyperfluoroethyl) hexanoic, 4-(bis(perfluoroisopropyl)fluoromethoxy)perfluorobutanoic, 4-(2-bis(perfluoroisopropyl)fluoromethoxyperfluoroethyl) butanoic, 2-(N-(ethyl)perfluorobutanesulfonamido)acetic, and 2-(N-(methyl)perfluorobutanesulfonamido)acetic, and the like, and mixtures thereof.

Preferred fluorine-containing monocarboxylic acids include 2-(N-(ethyl)perfluorobutanesulfonamido)acetic, 2-(N-(methyl)perfluorobutanesulfonamido) acetic, and the like, and mixtures thereof.

It will be understood, with respect to the above lists, that the terminal hydroxyl or carboxyl groups may be replaced with other functional groups Q' that are reactive with terminal acyl group (of the polyacyl compounds) or hydroxyl groups (of the polyol) to form the linking group Q of Formula I.

If desired, non-fluorinated monofunctional compounds, such as monoalcohol(s) or monocarboxylic acid(s) can be utilized in addition to the fluorine-containing monoalcohol (s) or monocarboxylic acid(s) as a portion of the total monoalcohol or monocarboxylic acid charge (for example, in amounts up to about 50 mole percent of the total).

The most preferred ester oligomers comprises the condensation reaction product of one or more fluorinated polyols, an excess amount (relative to the polyol) of one or more diacyl compounds, and sufficient fluorinated monoalcohols to react with the terminal acyl groups. Such most preferred oligomers correspond to the Formula $$R_fQ[C(O)—R^1—C(O)O—R^2O—]_n[C(O)—R^1—C(O)]_m—QR_f$$

wherein:

n is a number from 1 to 10 inclusive;

m is 1;

$R_f$ is a perfluoroalkyl group having 1 to 12, preferably 6 or fewer carbon atoms, or a perfluoroheteroalkyl group having 3 to about 50 carbon atoms with all perfluorocarbon chains present having 1 to 6, preferably 1 to 4 carbon atoms;

Q is a divalent linking group as previously described;

$R^1$ is a straight chain alkylene, of 1 to 14 carbon atoms. Optionally, $R^1$ may further comprise a water-solubilizing group or a polymerizable group;

$R_2$ is a polyvalent organic group which is a residue of the polyol, that is a straight or branched chain alkylene, cycloalkylene, arylene or heteroalkylene group of 1 to 14 carbon atoms, preferably 1 to 8 carbon atoms, more preferably 1 to 4 carbon atoms, and most preferably two carbon atoms, or an arylene group of 6 to 12 carbon atoms; at least a portion of $R^2$ groups are substituted with or contain one perfluoroalkyl group, perfluoroheteroalkyl group, perfluoroheteroalkylene group, or mixtures thereof. Optionally, $R^2$ may further comprise a water-solubilizing group or a polymerizable group.

The fluorochemical compositions may further comprise the reaction product of water-solubilizing compounds comprising one or more water-solubilizing groups and at least one group reactive with the hydroxy (of the polyol) or the acyl group (of the polyacyl compound).

The water-solubilizing groups of the water solubilizing compounds include, for example, carboxylate, sulfate, sulfonate, phosphate, phosphonate, ammonium, and quaternary ammonium groups. Such groups may be represented as $-CO_2M$, $-OSO_3M$, $-SO_3M$, $-PO(OM)_2$, $-P(OM)_3$, $-NR_2HX$, $-NR_3X$, $-NRH_2X$, and $-NH_3X$, respectively, wherein M is H or one equivalent of a monovalent or divalent soluble cation such as sodium, potassium, calcium, and $NR_3H^+$; X is a soluble anion such as those selected from the group consisting of halide, hydroxide, carboxylate, sulfonates, and the like; and R is selected from the group consisting of a phenyl group, a cycloaliphatic group, or a straight or branched aliphatic group having from about 1 to about 12 carbon atoms. Preferably, R is a lower alkyl group having from 1 to 4 carbon atoms. The group $-NR_3X$ is a salt of a water-soluble acid, for example trimethyl ammonium chloride, pyridinium sulfate, etc. or an ammonium substituent. The group $-NR_2HX$ is the salt of a water-soluble acid, such as dimethyl ammonium acetate or propionate. The group $-NRH_2X$ is the salt of a water-soluble acid, such as methyl ammonium acetate or propionate. The group $-NH_3X$ is the salt of a water-soluble acid, such as ammonium acetate or propionate. The salt form can be made by simple neutralization of the acid group with a base such as an amine, a quaternary ammonium hydroxide, an alkali metal carbonate or hydroxide, or the like; or alternatively by simple reaction of the amino group with a carboxylic acid, a sulfonic acid, a halo acid, or the like.

The water solubilizing group is incorporated into the fluorochemical ester compounds by means of a reactive group which is reactive with the hydroxy (of the polyol) or the acyl group (of the polyacyl compound).

Useful acyl reactive groups include those selected from the group consisting of $-OH$, $-SH$, $NH_2$, and $NRH$ wherein R is selected from the group consisting of a phenyl group, a cycloaliphatic group, or a straight or branched aliphatic group having from about 1 to about 12 carbon atoms. Preferably, R is a lower alkyl group having from 1 to 4 carbon atoms. A representative suitable diol with a solubilizing group is 1,1-bis(hydroxymethyl)propionic acid and its salts such as its ammonium salt. A representative suitable monoalcohol with a solubilizing group is glycolic acid ($HOCH_2COOH$) and its salts. The amount of water-solubilizing group should be sufficient to solubilize or allow dispersion of the fluorochemical composition. Typically, the ester:solubilizing group ratio should be from about 3:1 to about 16:1, preferably from about 5:1 to about 11:1. Similarly, the water-solubilizing group may be incorporated into the fluorochemical urethane oligomers by means of a hydroxyl-reactive group, such as electrophilic functional groups, as known in the art.

Illustrative water-solubilizing compounds having suitable water-solubilizing groups include, but are not limited to, those independently selected from the group consisting of $HOCH_2COOH$; $HSCH_2COOH$; $(HOCH_2CH_2)_2NCH_2COOH$; $HOC(CO_2H)(CH_2CO_2H)_2$; $(H_2N(CH_2)_nCH_2)_2NCH_3$ wherein n is an integer of 1 to 3; $(HOCH_2)_2C(CH_3)COOH$; $(HO(CH_2)_nCH_2)_2NCH_3$ wherein n is an integer of 1 to 3; $HOCH_2CH(OH)CO_2Na$; N-(2-hydroxyethyl)iminodiacetic acid ($HOCH_2CH_2N(CH_2COOH)_2$); L-glutamic acid ($H_2NCH(COOH)(CH_2CH_2COOH)$); aspartic acid ($H_2NCH(COOH)(CH_2COOH)$); glycine ($H_2NCH_2COOH$); 1,3-diamino-2-propanol-N,N,N',N'-tetraacetic acid ($HOCH(CH_2N(CH_2COOH)_2)_2$); iminodiacetic acid ($HN(CH_2COOH)_2$); mercaptosuccinic acid ($HSCH(COOH)(CH_2COOH)$); $H_2N(CH_2)_4CH(COOH)N(CH_2COOH)_2$; $HOCH(COOH)CH(COOH)CH_2COOH$; $(HOCH_2)_2CHCH_2COO^-(NH(CH_3)_3)^+$; $CH_3(CH_2)_2CH(OH)CH(OH)(CH_2)_3CO_2K$; $H_2NCH_2CH_2OSO_3Na$; $H_2NC_2H_4NHC_2H_4SO_3H$; $H_2NC_3H_6NH(CH_3)C_3H_6SO_3H$; $(HOC_2H_4)_2NC_3H_6OSO_3Na$; $(HOCH_2CH_2)_2NC_6H_4OCH_2CH_2OSO_2OH$; N-methyl-4-(2,3-dihydroxypropoxy)pyridinium chloride, $((H_2N)_2C_6H_3SO_3)^-(NH(C_2H_5)_3)^+$; dihydroxybenzoic acid; 3,4-dihydroxybenzylic acid; 3-(3,5-dihydroxyphenyl)propionic acid; salts of the above amines, carboxylic acids, and sulfonic acids; diol-amines of the general formula $R-N[(CH_2CH_2O)_xH][(CH_2CH_2O)y]H$, where x+y=2, 5, 10, 15 and 50, triol-amines of the general formula $R-N[(CH_2CH_2O)x]H-CH_2CH_2CH_2-N[(CH_2CH_2O)y]H[CH_2CH_2O)_zH]$, where x+y+z=3, 10, 15 and 50,and ammonium salts of the indicated triol- and diol-amines (where R is an alkyl, available from Akzo Chemical; acrylic and methacrylic acid; and mixtures thereof. An example of a water-solubilizing compound having a hydroxy-reactive functional group is $Br-(CH_2)_n-CO_2H$.

The fluorochemical compositions may further comprise the reaction product of polymerizable compounds comprising one or more polymerizable groups and at least one reactive group, reactive with hydroxyl or acyl groups. The polymerizable group may be incorporated into the fluorochemical ester oligomers by means of a reactive functional group, as previously described. Examples of useful polymerizable groups include but are not limited to acrylate, methacrylate, vinyl, allyl, and glycidyl. Representative useful compounds having polymerizable groups include hydroxyethyl acrylate, hydroxyethyl methacrylate, pentaerythriol triacrylate, allyl alcohol, glycidol, $C_2H_5(CH_3)C=N-OH$, $CH_2=CHO(CH_2)_4OH$ and glycidyl methacrylate.

The fluorochemical compositions of the present invention comprising a mixture of ester molecules can be made by simple blending of the polyol(s), monofunctional compound(s), polyacyl compound(s) and optionally (d) one or more water-solubilizing compounds or (e) one or more polymerizable compounds. As one skilled in the art would understand, the order of blending or the ordering of the steps is non-limiting and can be modified so as to produce a desired fluorochemical composition. In the synthesis, for example, the polyacyl compound(s), the polyol(s), the fluorine-containing monofunctional compound ($R_fQ'$), and optionally (d) one or more water-solubilizing compounds or (e) one or more polymerizable compounds and a solvent are charged to a dry reaction vessel in immediate succession or as pre-made mixtures. When a homogeneous mixture or solution is obtained a catalyst is typically added, and the reaction mixture is heated. The temperature is generally determined by the boiling point of the solvent, and the boiling point of the byproducts. Byproducts, such as water or alcohols are generally removed by azeotropic distillation.

When a fluorine-containing monofunctional compound ($R_fQ'$) is used to prepare fluorine-containing ester compounds and oligomers of Formula I above, the molar ratio of monofunctional compound to polyacyl compound can be in the range of about 1:1 to 1:10 (preferably, about 1:1 to 1:7; more preferably, about 1:1 to 1:2; and most preferably, about 1:1 to 1:1.5). The ratio of polyacyl compound to polyol can then be in the range of about 2:1 to 1:2. Preferably, the ratio of the total number of equivalents of hydroxyl groups to the total number of equivalents of acyl groups is about 1:1. A slight excess of either the polyacyl compound or polyol is preferred.

Depending on reaction conditions (e.g., reaction temperature and/or polyacyl compound used), a catalyst level of up to about 0.5 percent by weight of the polyacyl compound/polyol/monofunctional compound mixture may be used, but typically about 0.00005 to about 0.5 percent by weight is required, 0.02 to 0.1 percent by weight being preferred. Suitable catalysts include, those acid and base esterification catalysts such as are known in the art. Useful catalysts include Me-Ph-$SO_3$H and $CF_3SO_3$H. If an acid catalyst is used, it is preferably removed from the oligomer or neutralized after the oligomerization. It has been found that the presence of the catalyst may deleteriously affect the contact angle performance.

A mixture of polyols and/or a mixture of monofunctional compounds can be used instead of a single polyol and/or a single monofunctional compound. For example, a polyol mixture comprising a polyol with a water-solubilizing or a polymerizable group and a polyol with an $R_f$ group can be used. As well, a monofunctional compound mixture comprising a monofunctional compound with a water-solubilizing or polymerizable group and a fluorine-containing monofunctional compound can be used.

The fluorochemical compositions of the invention can be prepared by using procedures and apparatus known to those skilled in the art of esterification and ester exchange reactions. For example, the fluorochemical compositions can be prepared by (a) simultaneously reacting the fluorine-containing monofunctional compound with the polyol and the diacyl compound (or derivative); (b) first reacting the polyol with the polyacyl compound (or derivative), and then reacting the resulting mixture with the fluorine-containing monofunctional compound; or (c) first reacting either the fluorine-containing monofunctional compound with the diacyl compound (or derivative) or the fluorine-containing monofunctional compound with the polyol, and then reacting the resulting mixture with the remaining reactant. Method (b) is generally preferred, because the probability of complete consumption of the fluorine-containing reactant can be higher than for Methods (a) and (c), and because it is believed that this method can produce a broader range of oligomers than Methods (a) and (c).

The reactions can be carried out in solution or in the molten state (using commonly-used solvents and/or equipment), generally under atmospheric pressure and at temperatures sufficient to maintain the reactants in solution or in the melt. For example, melt temperatures in the range of about 90–240° C. (preferably, about 100–210° C.; more preferably, about 110–170° C.) can generally be utilized. Removal of solvent or byproduct HCl, if present, can be conducted at reduced pressures, for example, using a vacuum equivalent to 500 torr (67 kPa) or less. Removal of esterification byproducts by distillation may be effect by selection of an appropriate solvent, such as toluene or fluorinated ethers such as HFE-7100™ or HFE-7200™ (available from the 3M Company).

If water is a by-product, then water immiscible solvents such as toluene, fluorinated ethers or perfluorocarbons are preferred. If the byproducts are lower alcohols, then perfluorocarbons are preferred.

The fluorochemical compositions of the present invention comprising a mixture of ester compounds can also be made following a step-wise synthesis in addition to a batch method. In the synthesis, the polyacyl compound and the polyol are dissolved together under dry conditions, preferably in a solvent, and then the resulting solution is heated as previously described, with mixing in the presence of a catalyst for one-half to two hours, preferably one hour.

The resulting ester oligomers may then further reacted with one or more of the monofunctional compounds described above. The monofunctional compounds may be added to the above reaction mixture, and react(s) with the remaining or a substantial portion of the remaining hydroxyl or acyl groups. The above temperatures, dry conditions, and mixing are continued one-half to two hours, preferably one hour. Terminal fluorine-containing groups may thereby bonded to the hydroxyl or acyl functional ester oligomers and compounds. These oligomers and compounds can be optionally further functionalized with water-solublizing or polymerizable groups described above by reacting any of the remaining hydroxyl or acyl groups in the resulting mixture with one or more of the reactive water-solubilizing or polymerizable group-containing compounds described above. Thus, the water-solubilizing or polymerizable compound(s) is (are) added to the reaction mixture, using the same conditions as with the previous additions.

Water-solubilizing or polymerizable group-containing compounds can be added and reacted with hydroxyl or acyl groups under the conditions described above in any of the steps described above. For example, as mentioned above, the water-solubilizing or polymerizable group-containing compound can be added as a mixture with the polyol. Alternatively, the water-solubilizing or polymerizable group-containing compound can be added (a) after reaction of the polyol with the polyacyl compound, (b) as a mixture with the monoalcohol(s), and (c) after reaction of the polyol and monofunctional compound with the polyacyl compound. When the water-solubilizing or polymerizable group-containing compound is a monoalcohol, it is preferably added as a mixture with the fluorine-containing monoalcohol. When the water-solubilizing or polymerizable group-containing compound is a diol, it is preferably added as a mixture with the polyol.

When the chemical composition of the present invention contains an ester oligomer having one or more carboxylic acid groups, solubility or dispersability of the composition in water can be further increased by forming a salt of the carboxylic acid group(s). Basic salt-forming compounds, such as tertiary amines, quaternary ammonium hydroxides, and inorganic bases, including, but not limited to, those selected from the group consisting of sodium hydroxide, potassium hydroxide, cesium hydroxide, lithium hydroxide, calcium hydroxide, magnesium hydroxide, zinc hydroxide, and barium hydroxide, may be used in a sufficient amount (i.e., in an amount to maintain a pH of greater than about 6). These basic salt-forming compounds preferably can be added in the water phase, but optionally in the preparation of the ester oligomers, to form salts with the incorporated, pendant and/or terminal carboxylic acid groups on the ester oligomer. Examples of useful amine salt-forming compounds include, but are not limited to, those selected from the group consisting of ammonia, trimethyl amine, triethyl amine, tripropylamine, triisopropyl amine, tributylamine, triethanolamine, diethanolamine, methyldiethanolamine, morpholine, N-methylmorpholine, dimethylethanolamine, and mixtures thereof. Preferred salt forming compounds include those selected from the group consisting of ammonia, trimethylaamine, dimethylethanolamine, methyldiethanolamine, triethylamine, tripropylamine, and triisopropylamine, since the chemical compositions prepared therefrom are not excessively hydrophilic upon coating and curing. Since certain salts formed by the reaction of salt forming compounds, such as potassium hydroxide in combination with a carboxylic acid group, could result in undesired reaction with acyl groups, it is preferred to add the salt forming compound in a water phase after all of the diols, alcohol, and silane compounds have been reacted with the acyl groups of the polyacyl compound.

If desired for particular applications, small amounts of one or more polymeric or non-polymeric chain extenders (for example, diamines) can be utilized, in addition to the above-described reactants, in preparing the fluorochemical composition.

The coating compositions of the present invention comprise aqueous suspensions, emulsions, or solutions, or organic solvent (or organic solvent/water) solutions, suspensions, or emulsions comprising the fluorochemical compositions of the present invention. When applied as coatings, the fluorochemical coating compositions impart oil- and water-repellency properties, and/or stain-release and stain-resistance characteristics to any of a wide variety of substrates.

The fluorochemical compositions of the present invention can be dissolved, suspended, or dispersed in a variety of solvents to form coating compositions suitable for use in coating the chemical compositions of the present invention onto a substrate. Generally, the solvent solutions can contain from about 0.1 to about 50 percent, or even up to about 90 percent, by weight non-volatile solids (based on the total weight of the components). Aqueous suspensions, emulsions, or solutions are generally preferred and generally can contain a non-volatile solids content of about 0.1 to about 50 percent, preferably, about 1 to about 10 percent, by weight (based on the total weight of the components). Coating compositions preferably contain from about 0.1 to about 10 percent fluorochemical composition, based on the weight of the coating composition. Preferably the fluorochemical composition is used in the coating composition at about 1 to about 5 weight percent, most preferably from about 2 to about 3 weight percent. Suitable solvents include water, alcohols, esters, glycol ethers, amides, ketones, hydrocarbons, chlorohydrocarbons, hydrofluorocarbons, hydrofluoroethers, chlorocarbons, and mixtures thereof. Depending upon the substrate to which the composition is being applied, water is the preferred solvent because it does not raise any environmental concerns and is accepted as safe and non-toxic.

Another embodiment of the present invention is an article comprised of a substrate having one or more surfaces and on the one or more surfaces of this substrate is a cured coating derived from the coating composition of the present invention. After application and curing of the coating composition, the article displays high water and hexadecane dynamic receding contact angles, oil- and water-repellency, and/or stain-release and stain-resistance properties.

The coating compositions of the present invention can be applied to a wide variety of substrates, including, but not limited to, fibrous substrates and hard substrates. Fibrous substrates include woven, knit, and nonwoven fabrics, textiles, carpets, leather, and paper. Hard substrates include, but are not limited to, glass, ceramic, masonry, concrete, natural stone, man-made stone, metals, wood, plastics, and painted surfaces. Substrates can have flat or curved surfaces and may be particulate and fibrous in nature, as well. Preferred substrates are fibrous or are capable of imbibing a liquid and are therefore porous. Such substrates are particularly subject to staining and soiling, but also benefit greatly from the fluorochemical compositions of the present invention because the coating composition can penetrate into the fibrous or porous substrate surface and spread over the internal surfaces of the substrate.

Representative examples of substrates that can be coated with the coating composition include lenses used in ophthalmic spectacles, sunglasses, optical instruments, illuminators, watch crystals, and the like; plastic window glazing; signs; decorative surfaces such as wallpaper and vinyl flooring; composite or laminated substrates such as FORMICA™ brand sheeting or laminated flooring (e.g., PERGO™ brand flooring); ceramic tile and fixtures (sinks, showers, toilets); natural and man-made stones; decorative and paving stones; cement and stone sidewalks and driveways; particles that comprise grout or the finished surface of applied grout; wood furniture surface (desktops, tabletops); cabinet surfaces; wood flooring, decking, and fencing; leather; paper; fiber glass fabric and other fiber-containing fabrics; textiles; carpeting; drapery material, upholstery, clothing, and the like.

Since coatings prepared from the coating compositions can render metal surfaces resistant to soils, the optical properties of metal surfaces like those on decorative metal strips and mirrors can be preserved longer. The coating compositions can make wood surfaces more resistant to food and beverage stains while helping to maintain a lustrous appearance. In addition, the coating compositions can be applied as a protective coating on aircraft wings, boat hulls, fishing line, medical surfaces, and siding, and can be used in food release, mold release, adhesive release applications, and the like. Decorative stones include, for example, marble, granite, limestone, slate, and the like.

Preferred substrates that can be coated with the coating composition of the present invention are fibrous substrates, such as nonwoven, knits, and woven fabrics, carpet, drapery material, upholstery, clothing and essentially any textile. To impart repellency and/or stain-resistance characteristics to a substrate, having one or more surfaces, (a) the coating composition of the present invention is applied onto one or more surfaces of the substrate and (b) the coating composition is allowed to cure (i.e. dry) at ambient temperature or preferably at elevated temperatures. The use of elevated temperatures is particularly advantageous for curing fibrous substrates coated with the fluorochemical compositions of the present invention, since best repellency properties are then achieved. Elevated temperatures of 50 to 150° C. are preferred with 100 to 130° C. more preferred.

The coating compositions can be applied to a treatable substrate by standard methods such as, for example, spraying, padding, dipping, roll coating, brushing, or exhaustion (optionally followed by the drying of the treated substrate to remove any remaining water or solvent). The treatable substrate can be in the form of molded or blown articles, sheets, fibers (as such or in aggregated form, for example, yarn, toe, web, or roving, or in the form of fabricated textiles such as carpets), woven and nonwoven fabrics, films, etc. When coating flat substrates of appropriate size, knife-coating or bar-coating may be used to ensure uniform coatings of the substrate. If desired, the fluorochemical composition can be co-applied with conventional fiber treating agents, for example, spin finishes or fiber lubricants. Such a topical treatment process can involve the use of the neat fluorochemical composition, without added solvent, and is thus preferred from an environmental perspective over the use of organic solvent solutions of the fluorochemical composition.

The coating compositions can be applied in an amount sufficient to achieve the desired repellency properties for a particular application. This amount can be determined empirically and can be adjusted as necessary or desired to achieve the repellency properties without compromising the properties of the treatable substrate.

The coating compositions can be applied to a substrate in any desired thickness. Coatings as thin as a few microns can offer excellent low surface energy, stain-resistance, and stain-release. However, thicker coatings (e.g., up to about 20 microns or more) can also be used. Thicker coatings can be obtained by applying to the substrate a single thicker layer of a coating composition that contains a relatively high concentration of the chemical composition of the present invention. Thicker coatings can also be obtained by applying successive layers to the substrate of a coating composition that contains a relatively low concentration of the fluorochemical composition of the present invention. The latter can be done by applying a layer of the coating composition to the substrate and then drying prior to application of a successive layer. Successive layers of the coating can then be applied to dried layers. This procedure can be repeated until the desired coating thickness is achieved.

Another embodiment of the present invention is a water- and oil-repellent polymer composition prepared by (a) combining the repellency-imparting, fluorochemical composition and at least one thermoplastic polymer (optionally, along with other additives) and then melt processing the resulting combination; or (b) combining the repellency-imparting, fluorochemical composition and at least one thermosetting polymer or ceramer or the reactive precursors thereof (optionally, along with other additives) and then curing the resulting combination, optionally with the application of heat or actinic radiation. Alternative processes for preparing the polymer composition include, for example, (c) dissolving the repellency-imparting, fluorochemical composition and at least one treatable substrate (e.g., a polymer) in at least one solvent and then casting or coating (for example, on a substrate such as plastic sheet or film, fabric, wood, ceramic, or stone) the resulting solution and allowing evaporation of the solvent, optionally with the application of heat; and (d) combining the repellency-imparting, fluorochemical composition and at least one monomer (optionally, along with other additives) and then polymerizing the monomer, optionally in the presence of at least one solvent and optionally with the application of heat or actinic radiation.

To form a polymer melt blend by melt processing, the fluorochemical composition can be, for example, intimately mixed with pelletized or powdered polymer and then melt processed by known methods such as, for example, molding, melt blowing, melt spinning, or melt extrusion. The fluorochemical composition can be mixed directly with the polymer or it can be mixed with the polymer in the form of a "master batch" (concentrate) of the fluorochemical composition in the polymer. If desired, an organic solution of the fluorochemical composition can be mixed with powdered or pelletized polymer, followed by drying (to remove solvent) and then by melt processing. Alternatively, the fluorochemical composition can be injected into a molten polymer stream to form a blend immediately prior to, for example, extrusion into fibers or films or molding into articles.

After melt processing, an annealing step can be carried out to enhance the development of repellent characteristics. In addition to, or in lieu of, such an annealing step, the melt processed combination (for example, in the form of a film or a fiber) can also be embossed between two heated rolls, one or both of which can be patterned. An annealing step typically is conducted below the melt temperature of the polymer (for example, in the case of polyamide, at about 150–220° C. for a period of about 30 seconds to about 5 minutes).

The fluorochemical composition can be added to thermoplastic or thermosetting polymer (or, alternatively, to other treatable substrate materials) in amounts sufficient to achieve the desired repellency properties for a particular application. The amounts can be determined empirically and can be adjusted as necessary or desired to achieve the repellency properties without compromising the properties of the polymer (or other treatable substrate material). Generally, the fluorochemical composition can be added in amounts ranging from about 0.1 to about 10 percent by weight (preferably, from about 0.5 to about 4 percent; more preferably, from about 0.75 to about 2.5 percent) based on the weight of polymer (or other treatable substrate material).

Shaped articles can be made from the water- and oil-repellent composition of the invention, and such constructions will find utility in any application where some level of repellency characteristics is required. For example, the composition of the invention can be used to prepare films and molded or blown articles, as well as fibers (for example, melt-blown or melt-spun fibers, including microfibers and sheath-core fibers) that can be used to make woven, knit, and nonwoven fabrics. Such films, molded or blown articles, fibers, and fabrics exhibit water and oil repellency (and soil resistance) characteristics under a variety of environmental conditions and can be used in a variety of applications.

For example, molded articles comprising the composition of the invention can be prepared by standard methods (for example, by high temperature injection molding) and are particularly useful as, for example, headlamp covers for automobiles, lenses (including eyeglass lenses), casings or circuit boards for electronic devices (for example, computers), screens for display devices, windows (for example, aircraft windows), and the like. Films comprising the composition of the invention can be made by any of the film making methods commonly employed in the art. Such films can be nonporous or porous (the latter including films that are mechanically perforated), with the presence and degree of porosity being selected according to the desired performance characteristics. The films can be used as, for example, photographic films, transparency films for use with overhead projectors, tape backings, substrates for coating, and the like.

Fibers comprising the composition of the invention can be used to make woven, knit, or nonwoven fabrics that can be used, for example, in making medical fabrics, medical and industrial apparel, fabrics for use in making clothing, home furnishings such as rugs or carpets, paper machine clothing, and filter media such as chemical process filters or respirators. Nonwoven webs or fabrics can be prepared by processes used in the manufacture of either melt-blown or spunbonded webs. For example, a process similar to that described by Wente in "Superfine Thermoplastic Fibers," Indus. Eng'g Chem. 48, 1342 (1956) or by Wente et al. in "Manufacture of Superfine Organic Fibers," Naval Research Laboratories Report No. 4364 (1954) can be used. Multilayer constructions made from nonwoven fabrics enjoy wide industrial and commercial utility, for example, as medical fabrics. The makeup of the constituent layers of such multilayer constructions can be varied according to the desired end-use characteristics, and the constructions can comprise two or more layers of melt-blown and spunbonded webs in many useful combinations such as those described in U.S. Pat. Nos. 5,145,727 (Potts et al.) and 5,149,576 (Potts et al.), the descriptions of which are incorporated herein by reference. In multi-layer constructions, the fluorochemical composition can be used alone in one or more layers or can be used in combination with other additive(s) in one or more layers. Alternatively, the fluorochemical composition and the other additive(s) can each be independently segregated in one or more layers. For example, in a spunbonded/melt-blown/spunbonded ("SMS") three-layer construction, the other additive(s) (for example, antistats) can be used in one or both spunbonded layers, and the fluorochemical composition can be used in the melt-blown layer, to impart both antistatic and repellency characteristics to the overall construction.

The repellency-imparting, fluorochemical polymer composition can also find utility as an additive to coatings. Such coatings can be water- and oil-repellent, and scratch-resistant (as well as soil-resistant) and can be used in the photographic industry or as protective coatings for optical or magnetic recording media.

If desired, the water- and oil-repellent composition of the invention can further contain one or more additives, including those commonly used in the art, for example, dyes, pigments, antioxidants, ultraviolet stabilizers, flame retardants, surfactants, plasticizers, tackifiers, fillers, and mixtures thereof. In particular, performance enhancers (for example, polymers such as polybutylene) can be utilized to improve the repellency characteristics in, for example, melt additive polyolefin applications.

Objects and advantages of this invention are further illustrated by the following examples, but the particular materials and amounts thereof recited in these examples, as well as other conditions and details, should not be construed to unduly limit this invention. In the examples, where weight percent or parts by weight are indicated, these are based on the weight of the entire composition unless indicated otherwise.

EXAMPLES

Glossary

POSF—$C_8F_{17}SO_2F$, perfluorooctanesulfonyl fluoride, available as FLUORAD™ FX-8 fluorochemical intermediate from 3M Company, St. Paul, Minn.

PHSF—$C_6F_{13}SO_2F$, perfluorooctanesulfonyl fluoride, available as a fluorochemical intermediate from 3M Company.

PBSF—$C_4F_9SO_2F$, perfluorobutanesulfonyl fluoride, available from Sigma-Aldrich, Milwaukee, Wis.

MeFOSE—$C_8F_{17}SO_2N(CH_3)CH_2CH_2OH$, having an equivalent weight of 557, can be made in two stages by reacting POSF with methylamine and ethylenechlorohydrin, using a procedure essentially as described in Example 1 of U.S. Pat. No. 2,803,656 (Ahlbrecht et al.), or alternatively by reacting N-methylperfluorooctylsulfonamide with ethylene glycol carbonate, using the procedure essentially as described in Example 7 of U.S. Pat. No. 3,734,962 (Niederprum et at.).

MeFBSE—$C_4F_9SO_2N(CH_3)CH_2CH_2OH$, having an equivalent weight of 357, can be made in two stages by reacting PBSF with methylamine and ethylenechlorohydrin, using a procedure essentially as described in Example 1 of U.S. Pat. No. 2,803,656 (Ahlbrecht, et al.).

FOSEE—$C_8F_{17}SO_2N(C_2H_4OH)_2$, can be prepared by reacting $C_8F_{17}SO_2NH_2$ with ethylene chlorohydrin as described in Example 8 of U.S. Pat. No. 3,787,351 (Olson). $C_8F_{17}SO_2NH_2$ can be prepared by reacting POSF with an equimolar amount of $NH_3$.

FHSEE—$C_6F_{13}SO_2N(C_2H_4OH)_2$, can be prepared as described in Example 8 of U.S. Pat. No. 3,787,351 (Olson), except that an equimolar amount of $C_6F_{13}SO_2NH_2$ is substituted for $C_8F_{17}SO_2NH_2$. $C_6F_{13}SO_2NH_2$ can be prepared by reacting PHSF with an equimolar amount of $NH_3$.

FBSEE—$C_4F_9SO_2N(C_2H_4OH)_2$, can be prepared as described in Example 8 of U.S. Pat. No. 3,787,351 (Olson), except that an equimolar amount of $C_4F_9SO_2NH_2$ is substituted for $C_8F_{17}SO_2NH_2$. $C_4F_9SO_2NH_2$ can be prepared by reacting PBSF with an equimolar amount of $NH_3$.

HDO—hexanediol, $HO(CH_2)_6OH$, available from Sigma-Aldrich.

ADA—adipic acid, $HOOC(CH_2)_4COOH$, available from Sigma-Aldrich.

ADC—adipoyl chloride, $ClC(O)(CH_2)_4C(O)Cl$, available from Sigma-Aldrich.

SBA—suberic acid, $HOOC(CH_2)_6COOH$, available from Sigma-Aldrich.

AZA—azelaic acid, $HOOC(CH_2)_7COOH$, available from Sigma-Aldrich.

DDA—dodecanedioic acid, $HOOC(CH_2)_{10}COOH$, available from Sigma-Aldrich.

AA—acrylic acid, $CH_2=CHCOOH$, available from Sigma-Aldrich.

CA—citric acid, $HOOCCH_2CH(OH)(COOH)CH_2COOH$, 99+%, available from Sigma-Aldrich.

Dimer Acid—hydrogenated dimmer acid available from Aldrich.

PEG Diacid—$HOOCCH_2(OCH_2CH_2)_nOCH_2COOH$, molecular weight approximately 600, available from Aldrich.

pTSA—p-toluenesulfonic acid monohydrate, available from Sigma-Aldrich.

$CF_3SO_3H$—trifluoromethanesulfonic acid, available as FLUORAD™ FC-24 fluorochemical acid from 3M Company.

VAZO™ 64—2,2'-azobis(isobutyronitrile) initiator, available from E. I. duPont de Nemours, Wilmington, Del.

THF—tetrahydrofuran

EtOAc—ethyl acetate

TEST METHODS

Stain Test—Zanger Blue limestone tiles (available from Color Tile, Maplewood, Minn.) (30.5 cm by 30.5 cm by 1.0 cm thick) were divided into 6 sections (10.2 cm by 15.2 cm) and washed with water thoroughly and allowed to dry at room temperature overnight. A 5% solvent solution of the polyester of the invention to be evaluated was coated onto the surface by wiping twice with a paper towel saturated with the chemical composition. Each of the resulting treated tile sections was then allowed to dry at ambient laboratory temperature for at least 12 hours before testing.

A spot test was used to visually rate the ability of the treated tile sections to prevent a test fluid drop from staining the tile after a given exposure period. The following test fluids were used:

(1) Grape juice (GJ)
(2) Anti-freeze coolant (AFC)
(3) Used 10W30 motor oil (MO)
(4) Paul Masson™ Burgundy wine (WIN)
(5) Water saturated with Taster's Choice coffee (COF)
(6) STP™ heavy duty brake fluid (BF)
(7) Mazola™ corn oil (CO)
(8) Soy sauce(SS)

A drop of each of the test fluids was place on each of the treated tile sections. After 20–24 hours, the drops were removed by wiping with a clean, dry, paper towel, and the tile was washed and scrubbed with Dawn™ liquid dishwashing soap mixed at 6 weight percent with tap water and rinsed with tap water. The visual appearance of the spot where each drop of test fluid had been place was rated on a scale of 0–5 as shown below. A rating of 0 represented the best stain-release performance of a chemical composition treatment of the tile surface.

0=no visible stain

1=trace of stain visible

2=outline of drop barely visible

3=outline of drop visible

4=dark outline of drop

5=dark stain which has spread

A total rating summing the eight stain tests was also calculated to provide an overall stain resistance rating for the treated substrate. A smaller total rating indicates a more effective treatment.

Advancing and Receding Contact Angle Test—The Advancing and Receding Contact Angle Test provides a quick and precise prediction of the surface properties of a coating material. Advancing and Receding contact angle values measured with water and n-hexadecane using this test correlate well with fluid repellency values measured on fabrics and carpets.

To run this test, a solution, emulsion, or suspension (typically at about 3% solids) is applied to nylon film by dip-coating. The nylon film is prepared as follows. Nylon film is cut into 85 mm×13 mm rectangular strips. Each strip is cleaned by dipping into methyl alcohol, wiping with a KIMWIPE™ wiper (commercially available from Kimberly-Clark Corp., Neenah, Wis.), taking care not to touch the strip's surface, and allowing the strip to dry for 15 minutes. Then, using a small binder clip to hold one end of the strip, the strip is immersed in the treating solution, and the strip is then withdrawn slowly and smoothly from the solution. The coated film strip is tilted to allow any solution run-off to accumulate at the corner of the strip, and a KIMWIPE™ wiper is touched to the corner to pull away the solution buildup. The coated film strip is allowed to air dry in a protected location for a minimum of 30 minutes and then is cured for 10 minutes at 121° C.

After the treatment is dry and cured, the advancing and receding contact angles are measured using a CAHN Dynamic Contact Angle Analyzer, Model DCA 322 (a Wilhelmy balance apparatus equipped with a computer for control and data processing, commercially available from ATI, Madison, Wis.). The CAHN Dynamic Contact Angle Analyzer is calibrated using a 500 mg weight. An alligator clip is fastened to a piece of coated film strip about 30 mm long, and the clip and film piece are hung from the stirrup of the balance. A 30 mL glass beaker containing approximately 25 mL of water or n-hexadecane is placed under the balance stirrup, and the beaker is positioned so that the coated film strip is centered over the beaker and its contents but not touching the walls of the beaker. Using the lever on the left side of the apparatus, the platform supporting the beaker is carefully raised until the surface of water or n-hexadecane is 2–3 mm from the lower edge of the film strip. The door to the apparatus is closed, the "Configure" option is chosen from the "Initialize" menu of the computer, the "Automatic" option is chosen from the "Experiment" menu, and the computer program then calculates the time for a scan. The apparatus then raises and lowers the liquid so that the scan is taken (the advancing angle is measured as the liquid moves up and over the surface, while the receding angle is determined as the liquid moves down and away from the surface of the plastic film). The "Least Squares" option is then selected from the "Analysis" menu, and the average receding contact angle is calculated from the scan of the film sample. Three separate films are prepared for each material to be tested as previously described. The 95% confidence interval for the average of the 3 scans is typically about 1.2°. This procedure is repeated for water and n-hexadecane.

Examples 1–4 and Comparative Examples C1–C3

This series of experiments was run to show the overall improvement in advancing contact angles (ACA) and receding contact angles (RCA) against water and n-hexadecane demonstrated by suberic acid-derived polyester polymers when both pendant and terminal $C_4F_9$-groups were present, as compared when only pendant $C_4F_9$-groups or only terminal $C_4F_9$-groups were present.

In Comparative Example C1, contact angles were measured for 1/1 FBSEE/SBA, which contained pendant $C_4F_9$-groups only.

In Comparative Examples C2 and C3, contact angles were measured for 2/1 MeFBSE/SBA, which contained terminal $C_4F_9$-groups only. In Comparative Example C2, the polyester reaction was catalyzed using pTSA (I), whereas in Comparative Example C3, the polyester reaction was catalyzed using $CF_3SO_3H$ (II).

In Examples 1–4, FBSEE diol, contact angles were measured for MeFBSE alcohol and SBA diacid reacted at molar ratios to give two terminal $C_4F_9$-groups and 1, 2, 2 and 3 pendant $C_4F_9$-groups, respectively (the number of pendant groups is equal to the theoretical number of FBSEE diol units in the polyester). For Example 2, the polyester reaction product was not washed (I), while for Example 3, the polyester was twice washed with water (II).

Results from the contact angle measurements are shown in TABLE 1.

TABLE 1

| Ex. | Polyester Composition | Water: ACA, ° | Water: RCA, ° | n-hexadecane: ACA, ° | n-hexadecane: RCA, ° |
|---|---|---|---|---|---|
| C1 | 1/1 FBSEE/SBA | 112 | 95 | 75 | 69 |
| C2 | 2/1 MeFBSE/SBA (I) | 114 | 87 | 79 | 69 |
| C3 | 2/1 MeFBSE/SBA (II) | 103 | 77 | 64 | 29 |
| 1 | 1/2/2 FBSEE/MeFBSE/SBA | 119 | 98 | 79 | 67 |
| 2 | 2/2/3 FBSEE/MeFBSE/SBA (I) | 112 | 89 | 81 | 56 |
| 3 | 2/2/3 FBSEE/MeFBSE/SBA (II) | 122 | 107 | 79 | 74 |
| 4 | 3/2/4 FBSEE/MeFBSE/SBA | 120 | 100 | 79 | 74 |

The data in TABLE 1 show that polyesters containing both pendant and terminal $C_4F_9$-groups demonstrated overall higher contact angles when compared to the polyesters containing only pendant or only terminal $C_4F_9$-groups. Comparing Examples 2 and 3, contact angle results improved when the product was water-washed.

TABLE 1—Polyester Preparations

1/1 FBSEE/SBA—In a reaction flask equipped with stirrer, heater and condenser with water trap were reacted 1.885 g (5 mmol) of FBSEE and 0.871 g (5 mmol) of SBA in the presence of two drops of $CF_3SO_3H$ in 100 g of toluene. The resulting mixture was heated to reflux for 2 hours, and the formed water was removed until, from FTIR analysis, no more hydroxyl signal was observed. Then, 1 g of NaHCO$_3$ was added, and the mixture was stirred for another 10 minutes. The solid was removed by filtration and the obtained solution was rotary evaporated to strip off all the solvent. he residue solid was dissolved in EtOAc.

2/1 MeFBSE/SBA (I)—In a reaction flask equipped with stirrer, heater and condenser with water trap were reacted 3.57 g (10 mmol) of MeFBSE and 0.87 g (5 mmol) of SBA in 50 g of toluene containing 0.2 g of pTSA catalyst. The mixture was refluxed for 10 hours while removing the formed water. After removing the solids by filtration and removing the toluene using rotary evaporation, the residue solid was dissolved in EtOAc.

2/1 MeFBSE/SBA (II)—In a reaction flask equipped with stirrer, heater and condenser with water trap were reacted 3.57 g (10 mmol) of MeFBSE and 0.87 g (5 mmol) SBA in 100 g of toluene containing 2 drops of CF$_3$SO$_3$H catalyst. The resulting mixture was refluxed for 2 hours while removing the formed water. After removing the solids by filtration and removing the toluene using rotary evaporation, the residue solid was dissolved in EtOAc.

1/2/2 FBSEE/MeFBSE/SBA—In a reaction flask equipped with stirrer, heater and condenser with water trap were first reacted 7.54 g (20 mmol) FBSEE and 6.968 g (40 mmol) of SBA in 150 g of toluene containing 2 drops of CF$_3$SO$_3$H catalyst. The resulting mixture was refluxed for 2 hours while removing the formed water. Then, 14.30 g (40 mmol) of MeFBSE was added, and the mixture was refluxed for an additional 5 hours after which, from FTIR analysis, no more hydroxyl signal was observed. After cooling mixture down to room temperature, the resulting reaction product was washed with two 20 mL aliquots of deionized water, with the desired product remaining in the top organic layer. After using rotary evaporation to strip off all the toluene, the residue solid was dissolved in EtOAc.

2/2/3 FBSEE/MeFBSE/SBA—In a reaction flask equipped with stirrer, heater and condenser with water trap were reacted 1.758 g (5 mmol) of MeFBSE, 1.885 g (5 mmol) FBSEE and 1.305 g (7.5 mmol) of SBA in 100 g of toluene containing two drops of CF$_3$SO$_3$H. The resulting mixture was heated to reflux for four hours while removing the formed water. After reaction, a sample of the mixture was removed and isolated (I). The remaining mixture portion was washed with two 20 mL aliquots of deionized water. The isolated top organic solution containing purified product was then isolated (II).

3/2/4 FBSEE/MeFBSE/SBA—In a reaction flask equipped with stirrer, heater and condenser with water trap were reacted 2.262 g (6 mmol) of FBSEE, 1.428 g (4 mmol) of MeFBSE and 1.392 g (8 mmol) of SBA in 80 g of toluene containing 2 drops of CF$_3$SO$_3$H catalyst. The resulting mixture was refluxed for 2 hours while removing the formed water by Dean-Star trap until, from FTIR analysis, no more hydroxyl signal was observed. To the mixture was then added 0.75 g of CaO, and the neutralized mixture was stirred at 45° C. for 0.5 hour. The mixture was filtered to removed the solid and solvent was stripped from the resulting filtrate using rotary evaporation. The resulting solid was dissolved in THF.

Examples 5–13 and Comparative Examples C4–C7

This series of experiments was run to show the overall improvement in advancing contact angles (ACA) and receding contact angles (RCA) against water and n-hexadecane demonstrated by adipic acid-derived polyester polymers when both pendant and terminal C$_4$F$_9$-groups were present, as compared when only pendant C$_4$F$_9$-groups or only terminal C$_4$F$_9$-groups were present.

In Comparative Examples C4–C5, contact angles were measured for 1/1 FBSEE/ADA polyesters (using pTSA and CF$_3$SO$_3$H catalyst, respectively), which contained pendant C$_4$F$_9$-groups only.

In Comparative Example C6, contact angles were measured for 2/1 MeFBSE/ADA, which contained terminal C$_4$F$_9$-groups only.

In Comparative Example C7, contact angles were measured for 1/2/2 HDO/MeFBSE/ADA, which contained terminal C$_4$F$_9$-groups only as it was derived from a non-R$_f$ group containing diol, hexanediol.

In Example 5 and 6, contact angles were measured for 1/2/2 FBSEE/MeFBSE/ADA, made with bicarbonate treatment and with a water wash, respectively. This polymer theoretically contained one pendant C$_4$F$_9$-group and two terminal C$_4$F$_9$-groups.

In Example 5 and 6, contact angles were measured for 1/2/2 FBSEE/MeFBSE/ADA, made with bicarbonate treatment (I) and with a water wash (II), respectively. These polymers theoretically contained one pendant C$_4$F$_9$-group and two terminal C$_4$F$_9$-groups.

In Examples 7–11, contact angles were measured for 2/2/3 FBSEE/MeFBSE/ADA made using various catalysts, reaction times and derived from both adipic acid and adipoyl chloride. These polymers theoretically contained two pendant C$_4$F$_9$-groups and two terminal C$_4$F$_9$-groups.

In Examples 12 and 13, contact angles were measured for 3/2/4 FBSEE/MeFBSE/ADA made by reacting all ingredients at once (Ex. 12) and by first reacting the FBSEE diol with the ADA diacid, followed by reaction with the MeFBSE alcohol (Ex. 13). These polymers theoretically contained three pendant C$_4$F$_9$-groups and two terminal C$_4$F$_9$-groups.

Results from the contact angle measurements are shown in TABLE 2.

TABLE 2

| | | Water: | | n-hexadecane: | |
|---|---|---|---|---|---|
| Ex. | Polyester Composition | ACA, ° | RCA, ° | ACA, ° | RCA, ° |
| C4 | FBSEE/ADA (I) | 98 | 70 | 78 | 66 |
| C5 | FBSEE/ADA (II) | 107 | 75 | 74 | 71 |
| C6 | 2/1 MeFBSE/ADA | 107 | 68 | 63 | 33 |
| C7 | 1/2/2 HDO/MeFBSE/ADA | 104 | 85 | 79 | 70 |
| 5 | 1/2/2 FBSEE/MeFBSEE/ADA (I) | 119 | 99 | 79 | 70 |
| 6 | 1/2/2 FBSEE/MeFBSEE/ADA (II) | 120 | 95 | 80 | 70 |
| 7 | 2/2/3/ FBSEE/MeFBSE/ADA (I) | 95 | 76 | 79 | 68 |
| 8 | 2/2/3/ FBSEE/MeFBSE/ADA (II) | 104 | 75 | 64 | 27 |
| 9 | 2/2/3/ FBSEE/MeFBSE/ADA (III) | 120 | 103 | 80 | 74 |
| 10 | 2/2/3/ FBSEE/MeFBSE/ADA (IV) | 107 | 92 | 79 | 69 |
| 11 | 2/2/3/ FBSEE/MeFBSE/ADC | 113 | 91 | 73 | 55 |
| 12 | 3/2/4 FBSEE/MeFBSE/ADA (I) | 118 | 95 | 79 | 74 |
| 13 | 3/2/4 FBSEE/MeFBSE/ADA (II) | 95 | 75 | 81 | 70 |

The data in TABLE 2 show that, on the average, both advancing and receding contact angles against water and n-hexadecane are greater for the polyesters containing both pendant and terminal —C$_4$F$_9$ groups, as compared to the polyesters containing only pendant or only terminal groups. The average values for Examples 5–13 vs. Comparative Examples C4–C7 are as follows: water ACA: 110° vs. 104°;

water RCA: 89° vs. 75°; n-hexadecane ACA: 77° vs. 74°; n-hexadecane RCA: 64° vs. 60°.

TABLE 2—Polyester Preparations

1/1 FBSEE/ADA (I)—In a reaction flask equipped with stirrer, heater and condeser with water trap were reacted 3.77 g (10 mmol) of FBSEE and 1.46 g (10 mmol) of ADA in the presence of 0.01 g of pTSA in 100 g of toluene. After refluxing for 5 hours and continually removing the formed water, FTIR analysis showed almost no remaining hydroxyl groups. The toluene was removed by rotary evaporation and the residue solid was dissolved in acetone.

1/1 FBSEE/ADA (II)—In a reaction flask equipped with stirrer, heater and condenser with water trap were reacted 1.885 g (5 mmol) of FBSEE and 0.73 g of ADA in the presence of two drops of $CF_3SO_3H$ in 100 g of toluene. The mixture was heated to reflux for 2 hours, and the formed water was continually removed until no more hydroxyl signal was observed using FTIR analysis. Then, 0.5 g of $NaHCO_3$ was added, and the resulting mixture was stirred for 10 minutes, during which time the light yellow color disappeared. The mixture was filtered to remove all solid, the solvent was removed by rotary evaporation, and the residue solid was dissolved in EtOAc.

2/1 MeFBSE/ADA—In a reaction flask equipped with stirrer, heater and condenser with water trap were reacted 7.14 g (20 mmol) of MeFBSE and 1.46 g (10 mmol) of ADA in 200 g of toluene containing 2 drops of $CF_3SO_3H$ catalyst. The resulting mixture was refluxed for 2 hours while removing the formed water. The reaction mixture was treated with excess $NaHCO_3$. After removing the solids by filtration and removing the toluene using rotary evaporation, the residue polyester solid was dissolved in EtOAc.

1/2/2 HDO/MeFBSE/ADA—In a reaction flask equipped with stirrer, heater and condenser with water trap were reacted 1.190 g (10 mmol) of HDO and 2.927 g (20 mmol) of ADA in 100 g of toluene containing 2 drops of $CF_3SO_3H$ catalyst. The resulting mixture was refluxed for 2 hours while removing the formed water. Then 7.152 g (20 mmol) of MeFBSE was added, and the new resulting mixture was refluxed for an additional two hours. The reaction mixture was treated with $NaHCO_3$ at 60° C. for 0.5 hour. After removing the solids by filtration and removing the toluene using rotary evaporation, the residue solid was dissolved in EtOAc.

1/2/2 FBSEE/MeFBSE/ADA (I,II)—In a reaction flask equipped with stirrer, heater and condenser with water trap were first reacted 3.809 g (10.1 mmol) FBSEE and 2.923 g (20.1 mmol) of ADA in 100 g of toluene containing 2 drops of $CF_3SO_3H$ catalyst. The resulting mixture was refluxed for 1 hour while removing the formed water. Then 7.152 g (20 mmol) of MeFBSE was added, and the new resulting mixture was refluxed for another 4 hours, after which no hydroxyl signal was observed using FTIR analysis. The solution was then separated into two portions, (I) and (II). 1.0 g of $NaHCO_3$ was added to portion (I), and the resulting mixture was stirred for 0.5 hour. Rotary evaporation was used to strip off the toluene, and the residue solid from portion (I) was dissolved in EtOAc. Then portion (II) was washed twice with deionized water, the separated top organic layer containing product was stripped, then the resulting residue solid was dissolved in THF.

2/2/3 FBSEE/MeFBSE/ADA (I)—In a reaction flask equipped with stirrer, heater and condenser with water trap were reacted 1.885 g (5 mmol) of FBSEE, 1.785 g (5 mmol) of MeFBSE and 1.095 g (7.5 mmol) of ADA in 100 g of toluene containing 0.057 g of pTSA catalyst. The resulting mixture was refluxed for 10 hours while continually removing the formed water. FTIR analysis of the reaction mixture indicated a small amount of unreacted hydroxyl. Toluene was removed using rotary evaporation, and the residue solid was dissolved in acetone.

2/2/3 FBSEE/MeFBSE/ADA (II)—In a reaction flask equipped with stirrer, heater and condenser with water trap were reacted 3.73 g (10 mmol) of FBSEE, 3.57 g (10 mmol) of MeFBSE and 2.19 g (15 mmol) of ADA in 100 g of toluene containing 0.02 g of pTSA catalyst. The resulting mixture was refluxed for 5 hours while removing the formed water, after which no hydroxyl signal was detected using FTIR analysis. The toluene was then removed using rotary evaporation, and the residue solid was dissolved in THF.

2/2/3 FBSEE/MeFBSE/ADA (III)—In a reaction flask equipped with stirrer, heater and condenser with water trap were reacted 1.885 g (5 mmol) of FBSEE, 1.785 g (5 mmol) of MeFBSE and 1.095 g (7.5 mmol) of ADA in 120 g of toluene containing 2 drops of $CF_3SO_3H$ catalyst. The resulting mixture was refluxed for 4 hours while removing the formed water. The solution was then treated with $NaHCO_3$. After removing the solids by filtration and removing the toluene using rotary evaporation, the residue solid was dissolved in EtOAc.

2/2/3 FBSEE/MeFBSE/ADA (IV)—In a reaction flask equipped with stirrer, heater and condenser with water trap were reacted 11.435 g (30.33 mmol) of FBSEE, 10.736 g (30.07 mmol) of MeFBSE and 6.581 g (45.07 mmol) of ADA in 200 g of toluene containing 2 drops of $CF_3SO_3H$ catalyst. The reaction mixture was refluxed for 2 hours while continually removing the formed water, then was treated with $NaHCO_3$. After removing the solids by filtration and removing the toluene using rotary evaporation, the residue solid was dissolved in acetone.

2/2/3 FBSEE/MeFBSE/ADC—To a 100 mL flask equipped with stirrer, heater, distillation column and addition funnel were charged 1.555 g (10.7 mmol) of ADC and 50 g of toluene. Then from an additional funnel was added a solution of 2.677 g (7.1 mmol) FBSEE and 2.535 g (7.1 mmol) MeFBSE in 5 g of $CH_2Cl_2$ and 5 g EtOAc at room temperature over a ½ hour period. After addition, the solution was refluxed for 10 hours, after which, from FTIR analysis, no more hydroxyl signal was observed. Rotary evaporation was used to strip off the solvent, and the residue solid was dissolved in THF.

3/2/4 FBSEE/MeFBSE/ADA (I)—In a reaction flask equipped with stirrer, heater and condenser with water trap were reacted 2.262 g (6 mmol) of FBSEE, 1.428 g (4 mmol) of MeFBSE and 1.168 g (8 mmol) of adipic acid (AA) in 100 g of toluene containing two drops of $CF_3SO_3H$ catalyst. The resulting mixture was refluxed for 2 hours while continually removing the formed water. The reaction mixture was then treated with CaO at 60° C. for 0.5 hour. After removing the solids by filtration and removing the toluene using rotary evaporation, the residue solid was dissolved in EtOAc.

3/2/4 FBSEE/MeFBSE/ADA (II)—In a reaction flask equipped with stirrer, heater and condenser with water trap were first reacted 1.885 g (5 mmol) FBSEE and 1.468 g (10.05 mmol) of ADA in 120 g of toluene containing 2 drops of $CF_3SO_3H$ catalyst. The resulting mixture was refluxed for 1 hour while continually removing the formed water. Then 3.782 g (10 mmol) of additional FBSEE was added and the resulting mixture refluxed for an additional hour. Then 1.465 g (10 mmol) of ADA was added, and the new mixture was refluxed for one hour. Finally, 3.58 g (10 mmol) of MeFBSE was added, and the final mixture was refluxed for 5 hours. The reaction mixture was treated with $NaHCO_3$. After removing the solids by filtration and removing the toluene using rotary evaporation, the residue solid was dissolved in EtOAc.

Examples 14 and Comparative Examples C8–C10

This series of experiments was run to show advancing contact angles (ACA) and receding contact angles (RCA) against water and n-hexadecane demonstrated by polyester polymer containing pendant $C_4F_9$-groups and terminal $C_8F_{17}$-groups as compared to polyester polymers containing pendant $C_4F_9$—, $C_6F_{13}$- and/or $C_8F_{17}$-groups but no terminal $R_f$ groups.

In Comparative Examples C8, contact angles were measured for 1/1 FHSEE/ADA polyester, which contained pendant $C_6F_{13}$-groups only.

In Comparative Examples C9, contact angles were measured for 0.2/0.8/1.0 FHSEE/FBSEE/ADA polyester, which theoretically contained 20% pendant $C_6F_{13}$-groups and 80% pendant $C_4F_9$-groups.

In Comparative Example C10, contact angles were measured for 1/1 FOSEE/ADA, which contained pendant $C_8F_{17}$-groups only.

In Example 14, contact angles were measured for 2/2/3 FBSEE/MeFOSE/ADA, which theoretically contained two pendant $C_4F_9$-groups and two terminal $C_8F_{17}$-groups.

Results from the contact angle measurements are shown in TABLE 3.

TABLE 3

| Ex. | Polyester Composition | Water: ACA | Water: RCA | n-hexadecane: ACA | n-hexadecane: RCA |
|---|---|---|---|---|---|
| C8 | 1/1 FHSEE/ADA | 116 | 81 | 74 | 57 |
| C9 | 0.2/0.8/1 FHSEE/FBSEE/ADA | 123 | 81 | 72 | 48 |
| C10 | 1/1 FOSEE/ADA | 111 | 78 | 76 | 59 |
| 14 | 2/2/3/ FBSEE/MeFOSE/ADA | 118 | 102 | 82 | 77 |

The data in TABLE 3 show that the polyester of Example 14, containing pendant $C_4F_9$-groups and terminal $C_8F_{17}$-groups, exhibits superior contact angles to all of the comparative polyesters containing only pendant $R_f$-groups. Especially notable is the advantage in performance over the polyester of Comparative Example C10, which contains only the longer-chain $C_8F_{17}$-groups that one skilled in the art would expect to exhibit greater repellency.

TABLE 3—Polyester Preparations

1/1 FHSEE/ADA—In a reaction flask equipped with stirrer, heater and condenser with water trap were reacted 4.73 g (10 mmol) of FHSEE and 1.46 g (10 mmol) of ADA in the presence of two drops of $CF_3SO_3H$ in 100 g of toluene. The resulting mixture was heated to reflux for 5 hours while removing the formed water until no further hydroxyl signal was evident using FTIR analysis. The toluene was removed by rotary evaporation, and the residue solid was dissolved in THF.

0.2/0.8/1 FHSEE/FBSEE/ADA—In a reaction flask equipped with stirrer, heater and condenser with water trap were reacted 0.95 g (2 mmol) of FHSEE, 2.98 g (8 mmol) of MeFBSEE and 1.46 g (10 mmol) of ADA in the presence of 0.02 g of pTSA in 100 g of toluene. The mixture was heated to reflux for 5 hours while continually removing the formed water. The toluene was removed by rotary evaporation, and the residue solid was dissolved in EtOAc.

1/1 FOSEE/ADA—In a reaction flask equipped with stirrer, heater and condenser with water trap were reacted 5.876 g (10.55 mmol) of FOSEE and 1.47 g (10.6 mmol) of ADA in the presence of two drops of $CF_3SO_3H$ in 100 g of toluene. The resulting mixture was refluxed for 2 hours, and the formed water was removed until, from FTIR analysis, no more hydroxyl signal was observed. Then, 1 g of $NaHCO_3$ was added and the mixture was stirred for another 10 minutes. The solution was filtered to remove the solid and the obtained solution was rotary evaporated to strip off all the solvent. The residue solid was dissolved in EtOAc.

2/2/3 FBSEE/MeFOSE/ADA—In a reaction flask equipped with stirrer, heater and condenser with water trap were reacted 2.523 g (6.69 mmol) of FBSEE, 3.727 g (6.69 mmol) of MeFOSE and 1.473 g (10.09 mmol) of ADA in 150 g of toluene containing 2 drops of $CF_3SO_3H$ catalyst. The mixture was refluxed for 2 hours while continually removing the formed water. The reaction mixture was treated with $NaHCO_3$ at 70° C. for 0.5 hour. After removing the solids by filtration and removing the toluene using rotary evaporation, the residue solid was dissolved in EtOAc.

Examples 15, 16 and 9

This series of experiments was run to show advancing contact angles (ACA) and receding contact angles (RCA) against water and n-hexadecane demonstrated by polyester polymers containing two pendant and terminal $C_4F_9$-groups and derived from three different diacids: dodecanedioic acid (DDA, $HOOC(CH_2)_{10}COOH$, Example 15), azelaic acid (AZA, $HOOC(CH_2)_7COOH$, Example 16) and adipic acid (ADA, $HOOC(CH_2)_2COOH$, Example 9, taken from TABLE 2). All three polyesters were made in approximately the same scale using the same acid catalyst, $CF_3SO_3H$.

Results are presented in TABLE 4.

TABLE 4

| Ex. | Polyester Composition | Water: ACA, ° | Water: RCA, ° | n-hexadecane: ACA, ° | n-hexadecane: RCA, ° |
|---|---|---|---|---|---|
| 15 | 2/2/3 FBSEE/MeFBSE/DDA | 110 | 83 | 80 | 71 |
| 16 | 2/2/3 FBSEE/MeFBSE/AZA | 104 | 73 | 70 | 51 |
| 9 | 2/2/3 FBSEE/MeFBSE/ADA (I) | 120 | 103 | 80 | 74 |

The data in TABLE 4 show that all of the diacids impart high advancing and receding contact angles to the polyesters.

TABLE 4—Polyester Preparations

2/2/3 FBSEE/MeFBSE/DDA—In a reaction flask equipped with stirrer, heater and condenser with water trap were reacted 1.888 g (5 mmol) of FBSEE, 1.799 g (5 mmol) of MeFBSE and 1.730 g (7.5 mmol) of DDA in 100 g of toluene containing 2 drops of $CF_3SO_3H$ catalyst. The resulting mixture was refluxed for 2 hours while removing the formed water. Then the reaction mixture was treated with $NaHCO_3$ at 50° C. for 0.5 hour. After removing the solids by filtration and removing the toluene using rotary evaporation, the residue solid was dissolved in EtOAc.

2/2/3 FBSEE/MeFBSE/AZA—In a reaction flask equipped with stirrer, heater and condenser with water trap were reacted 1.890 g (5 mmol) of FBSEE, 1.788 g (5 mmol) of MeFBSE and 1.425 g (7.5 mmol) of AZA in 100 g of toluene containing 2 drops of $CF_3SO_3H$ catalyst. The mixture was refluxed for 2 hours while removing the formed water. The reaction mixture was treated with $NaHCO_3$ at 50° C. for 0.5 hour. After removing the solids by filtration and removing the toluene using rotary evaporation, the residue solid was dissolved in EtOAc.

2/2/3 FBSEE/MeFBSE/ADA (III)—In a reaction flask equipped with stirrer, heater and condenser with water trap were reacted 1.885 g (5 mmol) of FBSEE, 1.785 g (5 mmol)

of MeFBSE and 1.095 g (7.5 mmol) of ADA in 120 g of toluene containing 2 drops of $CF_3SO_3H$ catalyst. The resulting mixture was refluxed for 4 hours while removing the formed water. The solution was then treated with $NaHCO_3$. After removing the solids by filtration and removing the toluene using rotary evaporation, the residue solid was dissolved in EtOAc.

Example 17

This experiment was run to show advancing contact angles (ACA) and receding contact angles (RCA) against water and n-hexadecane demonstrated by a polyester polymer (MeFBSE/ADA/FBSEE-Acr) made by polymerizing an acrylate monomer containing one pendant $C_4F_9$-group, one terminal $C_4F_9$-group and one polymerizable group.

Results are presented in TABLE 5.

TABLE 5

| | | Water: | | n-hexadecane: |
|---|---|---|---|---|
| Ex. | Polyester Composition | ACA, ° | RCA, ° | ACA, ° | RCA, ° |
| 17 | MeFBSE/ADA/FBSEE-Acr | 117 | 99 | 79 | 70 | mer having pendant $C_8F_{17}$-groups but having no terminal $R_f$-groups, was evaluated.

For Examples 18–22, various polyesters of this invention, containing both pendant and terminal $C_4F_9$-groups, were evaluated. The polyesters were the same as evaluated earlier for advancing and receding contact angles in Examples 6, 3, 4, 10 and 15, respectively.

Using the earlier-described Staining Test, the staining agents employed were: anti-freeze coolant (AFC), grape juice (GJ), soy sauce (SS), used 10W30 motor oil (MO), Paul Masson™ Burgundy wine (WIN), water saturated with Taster's Choice coffee (COF), STP™ heavy duty brake fluid (BF) and Mazola™ corn oil (CO). For this test, a 5-point rating scale was used, with a rating of "0" indicates essentially no stain remaining and a rating of "5" indicating very poor stain resistance. A total is also presented, with a lower total indicating better overall stain resistance.

Results from these evaluations are presented in TABLE 6.

TABLE 6

| | | | Stain Resistance Rating To: | | | | | | | |
|---|---|---|---|---|---|---|---|---|---|---|
| Ex. | Polyester Composition | Total | AFC | GJ | SS | MO | WIN | COF | BF | CO |
| C11 | No treatment | 40 | 5 | 5 | 5 | 5 | 5 | 5 | 5 | 5 |
| C12 | FC-759 | 12 | 1 | 4 | 1 | 0 | 4 | 2 | 0 | 0 |
| 18 | 1/2/2 FBSEE/MeFBSEE/ADA (II) | 12 | 0 | 2 | 1 | 1 | 2 | 2 | 2 | 2 |
| 19 | 2/2/3 FBSEE/MeFBSE/SBA (II) | 15 | 0 | 1 | 2 | 2 | 2 | 1 | 4 | 3 |
| 20 | 3/2/4 FBSEE/MeFBSE/SBA | 19 | 1 | 3 | 3 | 2 | 3 | 1 | 3 | 3 |
| 21 | 2/2/3/FBSEE/MeFBSE/ADA (IV) | 10 | 0 | 3 | 1 | 1 | 2 | 1 | 2 | 0 |
| 22 | 2/2/3 FBSEE/MeFBSE/DDA | 7 | 0 | 2 | 0 | 1 | 2 | 1 | 1 | 0 |

The data in TABLE 5 show that the polyester acrylate polymer having pendant and terminal $C_4F_9$-groups demonstrates excellent advancing and receding contact angles.
TABLE 5—Polyester Preparations
1/1/1 MeFBSE/ADA/FBSEE-Acr—In a reaction flask equipped with stirrer, heater and condenser with water trap were reacted 3.57 g (10 mmol) of MeFBSE, 3.77 g (10 mmol) of FBSEE, 1.46 g (10 mmol) of ADA and 0.72 g (10 mmol) of AA in 100 g of toluene containing 2 drops of $CF_3SO_3H$ catalyst. The resulting mixture was refluxed for 4 hours while removing the formed water. Then, 0.005 g of VAZO™ 64 initiator was added, and the activated mixture was reacted at 65° C. for 10 hours. The reaction mixture was treated with excess CaO at 70° C. for 0.5 hours. After removing the solids by filtration and removing the toluene using rotary evaporation, the residue solid was dissolved in EtOAc.

Examples 18–22 and Comparative
Examples C11–C12

This series of experiments was run to illustrate that the polyesters of this invention are effective in imparting repellency to limestone, a hard porous substrate.

For Comparative Example C11, no polyurethane was evaluated (i.e., an untreated tile was evaluated for stain resistance).

For Comparative Example C12, FC-759 (available from 3M Company, St. Paul, Minn.), which contains a fluoropoly- The data in TABLE 6 show that the polyesters containing terminal and pendant $C_4F_9$-groups imparted comparable stain resistance to the FC-759 treatment, which contained pendant $C_8F_{17}$-groups. This is surprising as one skilled in the art would expect a treatment containing longer chain $C_8F_{17}$-groups to outperform a treatment containing shorter chain $C_4F_9$-groups.

Examples 23–29

In Examples 23–29, a variety of polyesters of this invention were synthesized and evaluated for advancing and receding contact angles vs. water and n-hexadecane.

Hydrophilic polyesters, having water-solubilizing groups (e.g., the polyoxyethylene diol-derived polyester of Example 23, the citric acid-derived polyester of Example 24, or the polyoxyethylene dicarboxylic acid-derived polyester of Example 25) are presented.

Conversely, very hydrophobic polyesters having long-chain hydrocarbon groups (e.g., the dimer acid-derived polyesters of Examples 26–29) are presented.

Results from the contact angle measurements are shown in TABLE 7.

Polyester Preparations

Example 23

2/1 .85/0.15/3 MeFBSE/FBSEE/75-H-1400/ADA—In a 100 mL three-neck flask equipped with stirrer, heater and condenser with Dean-Stark trap were reacted 17.43 g (46.2 mmol) of FBSEE, 9.31 g (3.8 mmol) of UCON 75-H-1400™ a polyoxyethylene diol, 17.65. g (49.4 mmol) of MeFBSE and 11.02 g (75.5 mmol) ADA in 250 g of toluene with 4 drops of $CF_3SO_3H$. The resulting mixture was heated to reflux under nitrogen for four hours while removing the formed water in the Dean-Stark trap. The catalyst was removed by addition of CaO (1 g) followed by filtration. The toluene was removed by rotary evaporation, and the residue solid was dissolved at 25% solids in THP.

Example 24

4/1/2 MeFBSE/FBSEE/CA—In a 100 mL three-neck flask equipped with stirrer, heater and condenser with Dean-Stark trap were reacted 3.77 g (10 mmol) of FBSEE, 14.28 g (40 mmol) of MCFBSB and 4.20 g (20 mmol) of citric acid in 200 g of toluene with 4 drops of $CF_3SO_3H$. The mixture was heated to reflux under nitrogen for 6 hours while removing the water formed in the Dean-Star trap. The catalyst was removed by addition of CaO (1 g) followed by filtration. The toluene was removed by rotary evaporation, and the obtained residue solid warn dissolved at 25% solids in EtOAc.

Example 25

2/2/2.7/0.3 MeFBSE/FBSEE/ADA/PEG Diacid—In a 100 mL three-neck flask equipped with stirrer, heater and condenser with Dean-Stark trap were reacted 19.61 g (52 mmol) of FBSEE, 18.596 g (52.1 in mol) of MeFBSE, 10.245 g (70.2 mmol) of ADA and 4.734 g (7.9 mmol) of PEG diacid in 350 g of toluene with 4 drops of $CF_3SO_3H$. The mixture was heated to reflux under nitrogen for 10 hours while removing the formed water in the Dean-Stir trap. The catalyst was removed by addition of CaO (1 g) followed by filtration. The toluene was removed by rotary evaporation, and the obtained residue solid was dissolved at 25% solids In EtOAc.

Example 26

2/2/2.8/0.2 MeFBSE/FBSEE/DDA/Dimer Acid—In a 100 mL three-neck flask equipped with stirrer, heater and condenser with Dean-Stark trap were reacted 15.2 g (40.3 mmol) of FBSEE, 14.5 g (40.6 mmol) of MeFBSE, 12.9 g (56 mmol) of DDA ($HOOC(CH_2)_{10}COOH$) and 2.3 g (4 mmol) of dimer acid in 300 g of toluene with 4 drops of $CF_3SO_3H$. The mixture was heated to reflux under nitrogen for 10 hours while removing the water formed in the Dean-Star trap. The catalyst was removed by addition of CaO (1 g) followed by filtration. The toluene was removed by rotary evaporation, and the obtained residue solid was dissolved at 25% solids in EtOAc.

Example 27

2/2/2.7/0.3 MeFBSE/FBSEE/ADA/Dimer Acid—In a 100 mL three-neck flask equipped with stirrer, heater and condenser with Dean-Stark trap were reacted 15.08 a (40 mmol) of FESEE, 14.28 g (40 mmol) of MeFBSE, 7.884 g (54 mmol) of ADA and 3.42 g (6 mmol) of dimer acid in 300 g of toluene with 4 drops of $CF_3SO_3H$. The mixture was heated to reflux under nitrogen for 10 hours while removing the water formed in the Dean-Star trap. After removing catalyst by addition of CaO (1 g) followed by filtration, a solid residue was obtained after removing the toluene by rotary evaporation. The solid was dissolved at 25% solids in EtOAc.

Example 28

2/2/2/1 MeFBSE/FBSEE/ADA/Dimer Acid—In a 100 ml three-neck flask equipped with stirrer, heater and condenser with Dean-Stark trap were reacted 15.2 g (40.3 mmol) of FBSEE, 14.2 g (39.8 mmol) of MeFBSE, 5.8 g (39.7 mmol) of ADA and 12.2 g (21.4 mmol) of dimer acid in 300 g of toluene with 4 drops of $CF_3SO_3H$. The mixture was heated to reflux under nitrogen for 10 hours while removing the water formed in the Dean-Star trap. After removing catalyst by addition of CaO (1 g) followed by filtration, a solid was dissolved at 25% solids in EtOAc.

Example 29

2/1/1/1 MeFBSE/FBSEE/ADA/Dimer Acid—In a 100 mL three-neck flask equipped with stirrer, heater and condenser with Dean-Stark trap were reacted 7.6 g (20.2 mmol) of FBSEE, 14.4 g (40.3 mmol) of MeFBSE, 2.92 g (20 mmol) of ADA and 12.5 g (20.24 mmol) of dimer acid in 300 g of toluene with 4 drops of $CF_3SO_3H$. The mixture was heated to reflux under nitrogen for 10 hours while removing the water formed in the Dean-Star trap. Agter removing catalyst by addition of CaO (1 g) followed by filtration, a solid residue was obtained after removing the toluene by rotary evaporation. The solid was dissolved at 25% solids in EtOAc.

I claim:

1. A fluorochemical ester composition comprising:
    one or more oligomers wherein each oligomer comprises
    (i) at least one fluorine-containing repeatable unit and
    (ii) at least one fluorine-containing terminal group, and
    wherein said oligomers comprise the condensation reaction product of:
    (a) one or more fluorinated polyols;
    (b) one or more polyacyl compounds; and
    (c) one or more monofunctional fluorine-containing compounds comprising a functional group that is reactive with the hydroxyl group of said polyol (a) or with the acyl group of the polyacyl compounds (b).

2. The oligomers of claim 1 further comprising the reaction product of one or more water-solubilizing compounds comprising one or more water solubilizing groups and at least one electrophilic or nucleophilic moiety, said solubilizing groups independently pendant from the repeating unit, or terminal portion.

3. The water solubilizing oligomers of claim 2 wherein said water-solubilizing group is selected from the group consisting of carboxylate, sulfate, phosphate, sulfonate, phosphonate, ammonium, and quaternary ammonium groups.

4. The oligomers of claim 1 further comprising the reaction product of one or more polymerizable compounds comprising one or more polymerizable groups and at least one electrophilic or nucleophilic moiety, said polymerizable groups independently pendant from the repeating unit, or terminal portion.

5. The polymerizable oligomers of claim 4, wherein said polymerizable groups are selected from the group consisting of acrylate, methacrylate, vinyl allyl, and glycidyl groups.

6. The oligomers of claim 1 of the formula

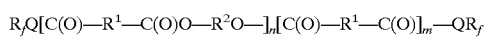

wherein:
n is a number from 1 to 10 inclusive;
m is 1;
$R_f$ is a perfluoroalkyl group having 1 to 12 carbon atoms, or a perfluoroheteroalkyl group having 3 to about 50 carbon atoms with all perfluorocarbon chains of said perfluoroheteroalkyl group having 1 to 6, preferably 1 to 4 carbon atoms;

Q is a divalent linking group;

$R^1$ is a straight chain alkylene, of 1 to 14 carbon atoms;

$R^2$ is a polyvalent organic group which is a residue of the polyol, that is a straight or branched chain alkylene, cycloalkylene, arylene or heteroalkylene group of 1 to 14 carbon atoms, or an arylene group of 6 to 12 carbon atoms;

at least a portion of $R^2$ groups comprise one perfluoroalkyl group, perfluoroheteroalkyl group, perfluoroheteroalkylene group, or mixtures thereof.

7. The composition of claim 1 wherein the oligomer comprises the condensation reaction product at one or more fluorinated polyols, one or more non-fluorinated polyols, one or more polyacyl compound and one or more monofunctional fluorine-containing compounds.

8. The composition of claim 1 wherein the oligomer comprises the condensation reaction product of one or more fluorinated polyols, an excess amount (relative to the polyol) or one or more linear alkylene diacyl compounds, and sufficient fluorinated monoalcohols to react with the terminal acyl groups.

9. The fluorochemical composition of claim 1 wherein the fluorine containing group of said polyol is a perfluoroalkyl group of 6 or fewer carbon atoms.

10. The fluorochemical composition of claim 1 wherein the fluorine containing group of said polyol is a perfluoroalkyl group of 3 to 5 carbon atoms.

11. The fluorochemical composition of claim 1 wherein the wherein the fluorine containing group of said polyol is a perfluoroalkyl group of is perfluorobutyl.

12. The oligomers of claim 1 of the formula $$R_fQ[OR^2]_o[-OC(O)-R^1-C(O)O-R^2O-]_n[C(O)-R^1-C(O)]_m-Z \quad (I)$$

wherein:

o is a number from 0 to 1 inclusive;

n is a number from 1 to 10 inclusive;

m is is number from 0 to 1 inclusive;

$R_f$ is a perfluoroalkyl group having 1 to 12 carbon atoms, or a perfluoroheteroalkyl group having 3 to about 50 carbon atoms with all perfluorocarbon chains of said perfluoroheteroalkyl group having 1 to 6 carbon atoms;

Q is a divalent linking group;

$R^1$ is a polyvalent organic groups that is a residue of a polyacyl compound, that is a straight or branched chain alkylene, cycloalkylene, or heteroalkylene group of 1 to 14 carbon atoms; or an arylene of 6 to 12 carbon atoms;

$R^2$ is a divalent organic group that is a residue of the polyol, at least a portion of which are substituted with or contain one or more perfluoroalkyl groups, perfluoroheteroalkyl groups, perfluoroheteroalkylene groups, or mixtures thereof; and Z is $R_fQ-$, a water-solubilizing group, or a polymerizable group.

13. The oligomer of claim 12, wherein Q is selected from the following structures, wherein each k is independently an integer from 0 to about 20, $R_1'$ is hydrogen, phenyl, or alkyl of 1 to about 4 carbon atoms, and R2 ' is alkyl of 1 to about 20 carbon atoms:

—$SO_2NR_1'(CH_2)_kO(O)C$—, —$CONR_1'(CH_2)_kO(O)C$—, —$(CH_2)_kO(O)C$—, —$CH_2CH(OR_2')CH_2O(O)C$—, —$(CH_2)kC(O)O$—, —$(CH_2)_kSC(O)$—, —$(CH_2)_kO(CH_2)_kO(O)C$—, —$(CH_2)_kS(CH_2)_kO(O)C$—, —$(CH_2)_k SO_2(CH_2)_kO(O)C$—, —$(CH_2)_kS(CH_2)_kOC(O)$—, —$(CH_2)_kSO_2NR_1'(CH_2)_kO(O)C$—, —$(CH_2)_k SO_2$—, —$SO_2NR_1'(CH_2)_kO$—, —$SO_2NR_1'(CH_2)_k$—, —$(CH_2)_kO(CH_2)_kC(O)O$—, —$(CH_2)_kSO_2NR_1'(CH_2)_kC(O)O$—, —$(CH_2)_kSO_2(CH_2)_kC(O)O$—, —$CONR_1'(CH_2)_kC(O)O$—, —$(CH_2)_kS(CH_2)_kC(O)O$—, —$CH_2CH(OR_2)CH_2C(O)O$—, —$SO_2NR_1'(CH_2)_kC(O)O$—, —$(CH_2)_kO$—, —$C_kH_{2k}$—$OC(O)NH$—, —$C_kH_{2k}$—$NR_1'C(O)NH$—, —$OC(O)NR'(CH_2)_k$—, —$(CH_2)_kNR_1'$— and —$(CH_2)_kNR_1'C(O)O$—.

14. The fluorochemical composition of claim 1 wherein the monofunctional fluorine-containing compound is a compound of the following formula I:

$$R_f-Q'$$

wherein:

$R_f$ is selected from the group consisting of perfluoroalkyl group having 1 to 12 carbon atoms, and perfluoroheteroalkyl group having 3 to about 50 carbon atoms with all perfluorocarbon chains present having 6 or fewer carbon atoms;

Q' is a functional group that is reactive with the terminal acyl group of the polyacyl group or terminal hydroxy group of the polyol.

15. The monofunctional fluorine-containing compound of claim 14 wherein Q' is selected from hydroxyl, secondary amino, oxazolinyl, oxazolonyl, acetyl, acetonyl, carboxyl, isocyanato, epoxy, aziridinyl, thio, ester and acyl halide groups.

16. The fluorochemical composition of claim 1 wherein said oligomers comprise the condensation reaction product of:

(a) one or more fluorinated polyols;

(b) one or more polyacyl compounds; and (c) one or more monofunctional fluorine-containing compounds comprising one functional group that is reactive with the hydroxyl group of said polyol (a) or with the acyl group of the polyacyl compound (b).

17. The fluorochemical composition of claim 16 wherein said fluorochemical oligomer further comprises the reaction product of one or more non-fluorinated polyols.

18. A coating composition comprising a mixture comprising:

(a) a solvent and (b) the fluorochemical composition of claim 1.

19. The coating composition of claim 18 wherein said mixture comprises an aqueous solution, dispersion or suspension.

20. The coating composition of claim 18 wherein the fluorochemical composition further comprises one or more water-solubilizing groups.

21. An article comprising a substrate having a coating of the fluorochemical composition of claim 1 on one or more surfaces of said substrate.

22. The article of claim 21 wherein the fluorochemical composition further comprises one or more water-solubilizing groups.

23. The article of claim 21 wherein the fluorochemical composition further comprises one or polymerizable groups.

24. The article of claim 21 wherein the substrate is selected from the group consisting of hard substrates and fibrous substrates.

25. A polymer composition comprising:
(a) the fluorochemical composition of claim 1; and
(b) at least one thermoplastic or thermoset polymer.

26. The polymer composition of claim 25 wherein said thermoplastic polymer is selected from the group consisting of polypropylene, polyethylene, polyacrylates, polymethacrylates, copolymers of ethylene and one or more alpha-olefins, polyesters, polyurethanes, polycarbonates, polyetherimides, polyimides, polyetherketones, polysulfones, polystyrenes, ABS copolymers, polyamides, fluoroplastics, and blends thereof; and said thermoset polymer is selected from the group consisting of polyurethanes, epoxy resins, fluoroelastomers, polyacrylates, polymethacrylates, and unsaturated polyesters, and blends thereof.

27. The polymer composition of claim 25 wherein said composition is prepared by forming a melt blend of said fluorochemical composition and said thermoplastic polymer.

28. A shaped article comprising the polymer composition of claim 25, wherein said shaped article is selected from fibers, films, and molded articles.

29. A process for preparing shaped article comprising the steps of
(a) combining the fluorochemical composition of claim 1 and at least one thermoplastic polymer; and
(b) melt processing the resulting combination.

30. A method of imparting repellancy to a substrate comprising the steps of: applying the coating composition of claim 18 onto one or more surfaces of said substrate; and curing the coating composition at ambient or elevated temperature.

* * * * *

UNITED STATES PATENT AND TRADEMARK OFFICE
CERTIFICATE OF CORRECTION

PATENT NO. : 6,753,380 B2
APPLICATION NO. : 09/803708
DATED : June 22, 2004
INVENTOR(S) : Zai-Ming Qiu It is certified that error appears in the above-identified patent and that said Letters Patent is hereby corrected as shown below:

Col. 20
Line 64, delete "trimethyl amine" and insert
-- trimethylamine --, therefor.
Lines 64-65, delete "triethyl amine" and insert
-- triethylamine --, therefor.
Line 65, delete "triisopropyl amine" and insert
-- triisopropylamine --, therefor.

Col. 21
Line 3, delete "trimethylaamine" and insert -- trimethylamine --, therefor.

Col. 22
Line 60, delete "yam" and insert -- yarn --, therefor.

Col. 31
Line 5, delete "condeser" and insert -- condenser --, therefor.

Col. 33
Line 9, delete "$R_f$ groups" and insert -- $R_f$- groups --, therefor.

Col. 36
Line 66, delete "2/1 .85/0.15/3" and insert -- 2/1.85/0.15/3 --, therefor.

Col. 37
Line 6, delete "refiux" and insert -- reflux --, therefor.
Line 10, delete "THP" and insert -- THF --, therefor.
Line 16, after "40" delete ")".
Line 16, delete "MCFBSB" and insert -- MeFBSE --, therefor.
Line 17, delete "toluone" and insert -- toluene --, therefor.
Line 22, delete "warn" and insert -- was --, therefor.
Line 30, delete "in mol" and insert -- mmol --, therefor.
Line 34, delete "Dean-Stir" and insert -- Dean-Star --, therefor.
Line 38, delete "In" and insert -- in --, therefor.
Line 58, delete "15.08 a" and insert -- 15.08 g --, therefor.
Line 59, delete "FESEE" and insert -- FBSEE --, therefor.

UNITED STATES PATENT AND TRADEMARK OFFICE
CERTIFICATE OF CORRECTION

PATENT NO. : 6,753,380 B2
APPLICATION NO. : 09/803708
DATED : June 22, 2004
INVENTOR(S) : Zai-Ming Qiu Page 2 of 2

It is certified that error appears in the above-identified patent and that said Letters Patent is hereby corrected as shown below:

Col. 38
Line 1, delete "ml" and insert -- mL --, therefor.
Line 10, after "solid" insert -- residue was obtained after removing the
 toluene by rotary evaporation. The solid --.
Line 21, delete "Agter" and insert -- After --, therefor.
Line 66, in Claim 6, delete "$\mathbf{R_r}$" and insert -- $\mathbf{R_f}$ --, therefor.

Col. 39
Line 16, in Claim 7, delete "at" and insert -- of --, therefor.
Line 23, in Claim 8, delete "or" and insert -- of --, therefor.

Col. 40
Line 1, in Claim 13, delete "$(CH_2)\mathbf{KC(O)O}$" and
 insert -- $(CH_2)_k C(O)O$ --, therefor.
Line 5, in Claim 13, delete "$SO_2NR_1'(CH_2)_k O$" and
 insert -- $SO_2NR_1'(CH_2)_k O$ --, therefor.
Line 9, in Claim 13, delete "$CH_2CH(\mathbf{OR_2})CH_2C(O)O$" and
 insert -- $CH_2CH(\mathbf{OR_2'})CH_2C(O)O$ --, therefor.

Col. 42
Line 11, in Claim 30, delete "repellancy" and
 insert -- repellency --, therefor.

Signed and Sealed this

Thirteenth Day of November, 2007

JON W. DUDAS
*Director of the United States Patent and Trademark Office*